United States Patent [19]

Kimura et al.

[11] Patent Number: 5,093,370

[45] Date of Patent: Mar. 3, 1992

[54] QUATERNARY AMMONIUM COMPOUNDS HAVING MUSCLE RELAXATION ACTIVITY

[75] Inventors: Masayasu Kimura, Toyama; Kenji Naito, Akishima; Osamu Sakuma, Tama; Tadashi Morita, Kashiwa, all of Japan

[73] Assignee: Tobishi Yakuhin Kogyo Kabushiki Kaisha, Tokyo, Japan

[21] Appl. No.: 506,862

[22] Filed: Apr. 9, 1990

[30] Foreign Application Priority Data

Apr. 10, 1989 [JP] Japan .................................. 1-87889

[51] Int. Cl.$^5$ ..................... A61K 31/04; C07D 295/02
[52] U.S. Cl. .................... 514/643; 564/290; 546/191; 546/264; 549/415; 549/22
[58] Field of Search .......... 564/290; 514/643

[56] References Cited

FOREIGN PATENT DOCUMENTS

| | | | |
|---|---|---|---|
| 558710A | 1/1948 | United Kingdom | 564/290 |
| 614763A | 12/1948 | United Kingdom | 564/281 |
| 685085A | 12/1952 | United Kingdom | 564/290 |
| 735631A | 8/1955 | United Kingdom | 564/281 |
| 742138A | 12/1955 | United Kingdom | 564/290 |
| 748224A | 4/1956 | United Kingdom | 564/290 |
| 751129A | 6/1956 | United Kingdom | 564/285 |
| 789448A | 1/1958 | United Kingdom | 564/281 |
| 1215521A | 12/1970 | United Kingdom | 556/42 |
| 2011388A | 7/1979 | United Kingdom | 564/284 |

*Primary Examiner*—Robert T. Bond
*Attorney, Agent, or Firm*—Ladas & Parry

[57] ABSTRACT

A quaternary ammonium having a muscle relaxation activity compound represented by the formula (I):

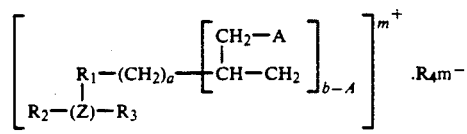

wherein $R_1$ represents a methylene, a lower alkylenoxy, a lower alkenylene, a lower alkynylene, —CO—, —COO—, a lower alkylene carbonyloxy, —CH(OR$_5$)—, a lower alkylenecarbonyl, a hydroxy lower alkylene, —O—, —S—, —SO—, or —SO$_2$—; $R_2$ represents a hydrogen atom, a hydroxy lower alkyl, an aldehyde, a lower alkyl carbonyl, —NO$_2$, or —NHR$_6$; $R_3$ represents a hydrogen atom of a group —R$_1$—(CH$_2$)$_a$—[CH(CH$_2$A)—CH$_2$]$_b$—A; R$_4$ represents an anion; R$_5$ and R$_6$ represent a hydrogen atom or a acetyl; A represents a quaternary ammonium group; a represents an integer of 1 to 8; b represents 0 or 1; m represents an integer of 1 to 4; and (Z) represents a trivalent benzene ring, a trivalent naphthalene ring, a trivalent diphenyl or a trivalent ethane radical.

4 Claims, No Drawings

QUATERNARY AMMONIUM COMPOUNDS HAVING MUSCLE RELAXATION ACTIVITY

BACKGROUND OF THE INVENTION

1. Field of the Invention

The present invention relates to novel quaternary ammonium compounds having a muscle relaxation activity, processes for a production thereof, and pharmaceutical preparations containing the compounds. The present compounds are useful for relaxing the muscle prior to the insertion of a trancheotomy tube or discission.

2. Description of the Related Art

Two types of muscle relaxants, i.e., the competitive (acetylcholine receptor antagonistic) type and the depolarizing type, are known. The competitive type agents include d-tubocurarine, pancuronium bromide, alcuronium chloride and the like, but only succinyl choline (suxamethonium) is used as the depolarizing type agent. The competitive type agents are commonly disadvantageous in that they do not have an immediate effect. The depolarizing type agents do have an immediate effect, but are disadvantageous in that they often induce temporary premature contraction upon administration, and provide postoperation muscle pain and muscle stress.

SUMMARY OF THE INVENTION

Accordingly, an object of the present invention is to provide depolarising type muscle relaxants which have an immediate effect and do not exhibit the above-mentioned drawbacks.

More specifically, the present invention provides a quaternary ammonium compound represented by the formula (I):

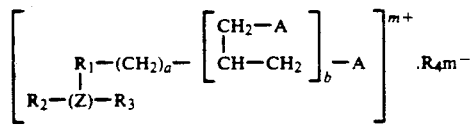

wherein $R_1$ represents a methylene, a lower alkyleneoxy, a lower alkenylene, a lower alkynylene, —CO—, —COO—, a lower alkylene carbonyloxy, —CH(OR$_5$)—, a lower alkylenecarbonyl, a hydroxy lower alkylene, —O—, —S—, —SO—, or —SO$_2$—;

$R_2$ represents a hydrogen atom, a hydroxy lower alkyl, an aldehyde, a lower alkyl carbonyl, NO$_2$, or —NHR$_6$;

$R_3$ represents a hydrogen atom or a group —R$_1$—(CH$_2$)$_a$—[CH(CH$_2$A)—CH]$_b$—A;

$R_4$ represents an anion;

$R_5$ and $R_6$ represent a hydrogen atom or acetyl;

A represents a quaternary ammonium group;

a represents an integer of 1 to 8;

b represents 0 or 1;

m represents an integer of 1 to 4; and (Z) represents a trivalent benzene ring, a trivalent naphthalene ring, a trivalent diphenyl or a trivalent ethane radical.

Moreover, the present invention provides a process for the production of the compound (I), comprising the step of reacting a compound represented by the formula (II):

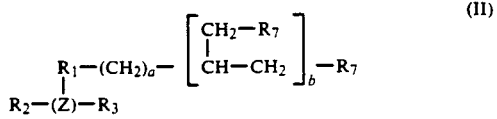

wherein the symbols have the same meanings as defined under the formula (I);

$R_3$ represents a hydrogen atom or a group —R$_1$—(CH$_2$)$_a$—[CH(CH$_2$R$_7$)—CH$_2$]$_b$—R$_7$;

$R_7$ represents a halogen atom or a reactive ester group such as sulfonyl group; and other symbols have the same meanings as defined above, with a tertiary amine.

The present invention also provides a process for the production of the compound (I) comprising the steps of reacting a tertiary amine represented by the formula (III):

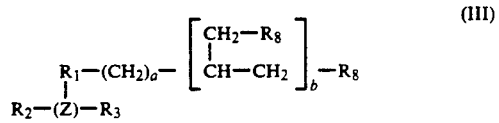

wherein $R_3$ represents a hydrogen atom or a group —R$_1$—(CH$_2$)$_a$—[CH(CH$_2$R$_8$)—CH$_2$]$_b$—R$_8$;

$R_8$ represents a tertiary amino group such as

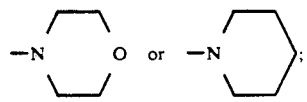

and other symbols have the same meanings as defined under the formula (I); with a haloalkyl or a reactive derivative of an alcohol.

The present invention still further provides a pharmaceutical preparation for muscle relaxation comprising the compound (I) together with a conventional pharmaceutical carrier.

DESCRIPTION OF THE PREFERRED EMBODIMENTS

To obtain desirable compounds satisfying the above-mentioned requirements, the present inventors synthesized various quaternary ammonium compounds having different distances between the ammonium groups, kinds of substituents, and types of chain moieties.

In the compound (I), an anion which forms a quaternary ammonium is, for example, an inorganic ion such as chloride, bromide, iodide, sulfate, sulfite or phosphate, or an organic ion such as tosylate, citrate, succinate, acetate, malate, or the like. Compounds in the form of such salts are advantageously easily isolated and purified, and have superior pharmacological effects and a simple formulation.

In the formula (I), the quaternary ammonium group A is formed from, for example, trialkyl ammonium such as trimethyl ammonium, triethyl ammonium; methyl diethyl ammonium or tripropyl ammonium; a saturated cyclic ammonium such as N-methylmorpholino, N-methylmorpholino or tropine derivatives; unsaturated cyclic ammonium such as pyridino, quinolino or thiazolino; or the like.

The lower alkyleneoxy $R_1$ is, for example, methyleneoxy, ethyleneoxy or propyleneoxy.

The lower alkenylene $R_1$ is, for example, vinylene group or propenylene group.

The lower alkynylene $R_1$ is, for example, ethynylene group.

The lower alkylene carbonyloxy $R_1$ is, for example, methylenecarbonyloxy, ethylenecarbonyloxy or propylenecarbonyloxy.

The lower alkylenecarbonyl $R_1$ is, for example, methylenecarbonyl, ethylenecarbonyl, propylenecarbonyl or isopropylenecarbonyl.

The hydroxy lower alkylene $R_1$ is, for example, ethylene having a hydroxy at a 2-position relating to (Z), and propylene having a hydroxy at 3-position relating to (Z).

The hydroxy lower alkyl $R_2$ is, for example, hydroxymethyl, 1-hydroxyethyl, 2-hydroxyethyl, 1-hydroxypropyl, 2-hydroxypropyl, 3-hydroxypropyl, 1-hydroxybutyl, 2-hydroxybutyl or the like.

The lower alkylcarbonyl $R_2$ is, for example, methylcarbonyl, ethylcarbonyl, propylcarbonyl, isopropylcarbonyl, or the like.

In a preferred embodiment, R represents $-CH_2-$, $-CH_2O-$, $-C\equiv C-$, $-CO-$, $-COO-$, $-CH_2CH_2COO-$, $-CH(OR_5)-$, $-CH_2CO-$, $-CH_2CH(OH)-$, $-O-$, $-S-$, $-SO-$ or $-SO_2-$; and $R_2$ represents $-H$, $-CH_2OH$, $-CH(CH_3)OH$, $-CH_2H_5)OH$, $-CHO$, $-COC_2H_5$, $-NO_2$ or $-NHR_6$.

According to an embodiment (A) for the production of the compound (I), a compound represented by the formula (II):

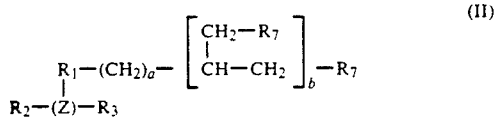

wherein $R_7$ represents a halogen such as fluorine, chlorine, bromine or iodine atom, or a reactive ester such as p-toluene sulfonyloxy, methansulfonyloxy, benzene sulfonyloxy, or sulfonyloxy, is reacted with a corresponding tertiary amine.

According to another embodiment (B), a tertiary amine represented by the formula (III):

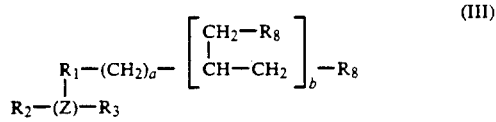

wherein $R_8$ represents a tertiary amine radical is reacted with haloalkyl or a reactive derivative, such as reactive ester, of an alcohol.

In the embodiment (A), the starting material (II) can be prepared by reacting an alcohol represented by the formula (IV):

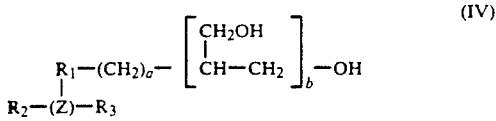

wherein all symbols have the same meaning as defined under the formula (I), with a halogenation agent or an esterification agent.

The halogenation agent is, for example, phosphorus tribromide, hydrogen bromide, phosphorus pentabromide, triphenylphosphite/cloline, triphenylphosphine/carbon tetrabromide, thionyl bromide, hydrogen chloride, phosphoryl chloride, phosphorus trichloride, phosphorus pentachloride, triphenylphosphite/bromine, triphenylphosphine/carbon tetrachloride, thionyl chloride, or the like.

The esterification agent is, for example, p-toluenesulfonyl chloride, methanesulfonyl chloride or sulfonyl unhydride thereof.

The reaction of the starting material (IV) and the halogenating agent or esterification agent is carried out in the absence of a solvent, or preferably in the presence of a solvent, for example, methylene chloride, chloroform, carbon tetrachloride, benzene, toluene, ether such as ethyl ether or dioxane, tetrahydrofuran, pyridine, triethylamine, or the like.

The esterification reaction is carried out, optionally in the presence of a dehalogenating agent, for example, an organic base such as triethylamine or pyridine, preferably, at a temperature between a room temperature and 100° C., for 1 to 2 hours.

In the reaction of a compound (II) with a tertiary amine, the tertiary amine is selected in accordance with the quaternary ammonium moiety A, and is, for example, trialkylamine such as trimethylamine, triethylamine, methyl diethyl amine or tripropylamine; a saturated cyclic amine, such as N-lower alkylpiperidine such as N-methylpiperidine, N-lower alkylmorpholine such as N-methylmorpholine, or tropine derivatives; a unsaturated cyclic amine such as pyridine, quinoline or thiazoline; or the like.

The reaction of the compound (II) with the tertiary amine is carried out in the absence of a solvent, or preferably, in the presence of a solvent, for example, an alcohol such as methanol or ethanol, halogenated alkane such as methylene chloride or carbon tetrachloride, or dimethylformamide, or other conventional solvent, at a temperature between a room temperature and 100° C., for 1 to 20 hours.

Note, the starting compounds (IV) are known or can be prepared by conventional procedures known per se, for example, by the procedures described in the Reference Examples.

In the embodiment (B), the starting material (III) can be prepared by reacting the active compound (II) described above with a corresponding secondary amine.

The secondary amine is selected in accordance with the quaternary ammonium portion A in the formula (I), and is, for example, di-lower alkylamine such as dimethylamine, diethylamine or methyl ethylamine, a saturated cyclic amine such as piperadine, morpholine, or pyridine.

The reaction of the compound (II) with the secondary amine is carried out in the absence of a solvent, or preferably in the presence of a solvent, for example, an alcohol such as methanol or ethanol, ether such as ethyl ether or tetrahydrofuran, haloalkyl such as methylene chloride or chloroform, ketone such acetone, dimethyl holmamide, or a mixture thereof with water, at a temperature between a room temperature and 100° C., for 1 to 20 hours.

In the reaction of the compound (III) with a haloalkyl or a reactive derivative of an alcohol, the haloalkyl and reactive derivative of alcohol are selected in accordance with the quaternary ammonium moiety A in the formula (2).

The haloalkyl is, for example, methyl iodide, ethyl iodide, propyl iodide, ethyl bromide, propyl iodide; the reactive derivative of alcohol is, preferably reactive ester of a corresponding alcohol, for example, sulfonate ester, such as methane sulfonate ester, benzenesulfonate ester, p-toluene sulfonate ester or the like.

The reaction of the compound (III) and the haloalkyl or reactive derivative of alcohol is carried out in the absence of a solvent, or preferably in the presence of a solvent, such as, an alcohol such as methanol or ethanol, haloalkyl such as methylene chloride or chloroform, or dimethylformanide, at a temperature between a room temperature and 100° C., for 1 to 20 hours.

EXAMPLES

The present invention will now be further illustrated by, but is no means limited to, the following Examples and Reference Examples.

In the Examples and Reference examples, the melting point was measured by a melting point analyzer, Yamato MP-21 (Yamato Kagaku, Japan) by a capillary method (not calibrated); the $^1$H—NMR was measured by a nuclear magnetic resonance analyzer JEOL.JNM-EX200 (Nippon Denshi, Japan; and the molecular weight was determined by a JMS-D300 type mass spectrometer (Nippon Denshi, Japan).

EXAMPLES

The present invention will now be further illustrated by, but is by no means limited to, the following Examples and Reference Examples.

REFERENCE EXAMPLE 1

1,4-Bis(4-hydroxybutyl)benzene

First, 16.5 g of p-diiodobenzene and 8.0 g of 3-butyn-1-ol were dissolved in 200 ml of triethylamine, 0.35 g of bis(triphenylphosphine)palladium (II) chloride and 0.19 g of cuprous iodide were added thereto, and the reaction mixture was stirred under nitrogen gas flow at a room temperature for 3 hours. After the reaction was completed, an insoluble matter was filtered off and the filtrate was evaporated under a reduced pressure. To the residue was added a small amount of ethyl acetate, which was then evaporated under a reduced pressure. To the residue was added water, and the mixture was extracted with 100 ml of ethyl acetate. The extract was washed with a saturated sodium chloride aqueous solution and dried over magnesium sulfate. On the other hand the insoluble matter obtained above was acidified with 1N HCl and extracted with 100 ml of ethyl acetate, and the extract was washed with a saturated sodium chloride aqueous solution and dried over magnesium sulfate. This ethyl acetate layer was combined with the ethyl acetate layer obtained above, and the mixture was evaporated under a reduced pressure to obtain 10.2 g of 1,4-bis(4-hydroxy-1-butynyl)benzene as a yellow residue.

10.2 g of the yellow residue obtained as above was dissolved in 300 ml of methanol, and 3.0 g of 5% palladium on carbon was added therein. The catalytic reduction was carried out at a room temperature under a atmospheric pressure. When 4.3 l of hydrogen was absorbed after 2 hours, the reaction was terminated, catalyst was filtered off, and the solvent was removed under a reduced pressure. To the residue was added water, the mixture was extracted with 100 ml of chloroform, and the extract was washed with a saturated sodium chloride aqueous solution and dried over magnesium sulfate. The solvent was removed under a reduced pressure to obtain 11.5 g of 1,4-bis(4-hydroxybutyl)benzene as a pale yellow crystal.

$^1$H—NMR (CDCl$_3$, δ ppm): 1.40–1.79 (10H, m), 2.61 (4H, t, J=7 Hz), 3.52–3.71 (4H, m), 7.11 (4H, s).

REFERENCE EXAMPLE 2

1,4-Bis(4-bromobutyl)benzene

To 11.5 g of 1,4-bis(4-hydroxybutyl)benzene was added 7.05 g of phosphorous tribromide under ice-cooling, and the mixture was stirred for 2 hours at 80° C. To the reaction mixture was added ice, and after dissolution and salting-out, the reaction mixture was extracted with 100 ml of chloroform, washed with a saturated sodium chloride aqueous solution and dried over magnesium sulfate, and the solvent was removed under a reduced pressure to obtain 15.2 g of a residue. The residue was then applied to a silica gel column and eluted with chloroform to obtain a first fraction, from which 13.1 g of 1,4-bis(4-bromobutyl)benzene was obtained as a pale yellow crystal.

$^1$H—NMR (CDCl$_3$, δ ppm): 1.65–1.99 (8H, m), 2.63 (4H, t, J=8 Hz), 3.43 (4H, t, J=7 Hz), 7.11 (4H, s).

REFERENCE EXAMPLE 3

1,4-Bis(4-dimethylaminobutyl)benzene

To 20 ml of ethanol were added 3.48 g of 1,4-bis(4-bromobutyl)benzene and 9 ml of 50% dimethylamine, and the mixture was stirred at a room temperature for 3.5 hours. After removing the solvent under a reduced pressure and adding chloroform, the mixture was then evaporated under a reduced pressure and added water, and the mixture was acidified with 1N hydrochloric acid and washed with chloroform. After alkalizing with 10% sodium hydroxide and salting-out, it was extracted with 100 ml of chloroform, washed with water and a saturated sodium chloride aqueous solution, dried over magnesium sulfate, and removed the solvent under a reduced pressure to obtain 2.70 g of a desired compound as a pale yellow liquid.

$^1$H—NMR (CDCl$_3$, δ ppm): 1.36–1.80 (8H, m), 2.09–2.38 (12H+4H, m), 2.61 (4H, t, J=7 Hz), 7.10 (4H, s).

EXAMPLE 1

1,4-Bis(4-trimethylammoniobutyl)benzene diiodide 3.1 g of 1,4-bis(4-dimethylaminobutyl)benzene and 7.2 g of methyl iodide were dissolved in 50 ml of absolute methanol, and the reaction mixture was heat to reflux for 2.5 hours. After the reaction was completed, the mixture was evaporated under a reduced pressure. To resulting crystal was added methanol, and the crystal was collected by filtration, washed with acetone, and dried under a reduced pressure to obtain 3.47 g of a desired compound as a pale yellow crystal.

Melting point: 245° C.;

$^1$H—NMR (DMSO-d6, δ ppm): 1.40–1.81 (8H, m), 2.59 (4H, t, J=7 Hz), 3.07 (18 H, s), 3.21–3.39 (4H, m), 7.15 (4H, s).

REFERENCE EXAMPLE 4

1,4-Bis(3-dimethylaminopropyloxy)benzene

First, to a solution of 2.3 g of metallic sodium dissolved in 35 ml of absolute methanol, a solution of 2.2 g of hydroquinon in 15 ml of absolute methanol and a solution of 7.9 g of 3-dimethylaminopropyl chloride hydrochloride in 10 ml absolute methanol were added, and the mixture was heated to reflux for 5 hours. After the reaction was completed, the mixture was evaporated under a reduced pressure, and after adding water to the resulting residue, alkalized with 10% sodium hydroxide, salted-out with sodium chloride and extracted with 100 ml of chloroform, the extract was washed with a saturated sodium chloride, and dried over magnesium sulfate. The solvent was removed under a reduced pressure to obtain a reddish liquid, which was dissolved in 1N hydrochloric acid, the solution was washed with chloroform, alkalized with 1N sodium hydroxide and extracted with 100 ml of chloroform. The extract was washed with a saturated sodium chloride aqueous solution and dried over magnesium sulfate, and the solvent was evaporated off under a reduced pressure to obtain 0.60 g of a desired compound as a reddish brown liquid.

$^1$H—NMR (CDCl$_3$, δ ppm): 1.93 (4H, m), 2.28 (12H, s), 2.48 (4H, t, J=8 Hz), 3.98 (4H, t, J=7 Hz), 6.82 (4H, s).

REFERENCE EXAMPLE 5

1,4-Bis(3-trimethylammoniopropyloxy)benzene diiodide

First, 0.6 g of 1,4-bis(3-dimethylaminopropyloxy)benzene and 4.2 g of methyl iodide were dissolved in 20 ml of absolute methanol, and the solution was heated to reflux for 2 hours. After the reaction was completed, the reaction mixture was cooled to a room temperature, and the resulting crystal was collected by filtration, washed with methanol and dried in vacuo to obtain 0.7 g of a pale yellow product.

Melting point: 255° C.;

$^1$H—NMR (DMSO-d6, δ ppm): 2.03-2.25 (4H, m), 3.12 (18H, s), 3.41-3.59 (4H, m), 4.02 (4H, t, J=6 Hz), 6.93 (4H, s).

REFERENCE EXAMPLE 6

1,4-Bis(4-dimethylaminobutyryl)benzene

Under nitrogen flow, to 70 ml of absolute tetrahydrofuran was added 1.58 g of metallic magnesium, followed by dropwise addition of 1.13 g of 1,2-dibromoethane. On a start of reaction, a solution of 7.0 g 3-(N,N-dimethylamino)propyl chloride in 30 ml of absolute tetrahydrofuran was added dropwise, and the mixture was heated to reflux for 1 hour. On the other hand, under nitrogen flow 5.74 g of terephthaloyl dichloride was dissolved in 30 ml of absolute tetrahydrofuran, the solution was cooled to −70° C. with dry ice/methanol, and after the above-prepared solution of Grignard reagent in tetrahydrofuran was added dropwise over 2 hours, the mixture was stirred overnight. To this reaction mixture were added methanol and 1N hydrochloric acid to dissolve solid materials, the organic solvent was removed under a reduced pressure, and the residual aqueous layer was acidified with 6N hydrochloric acid, washed with chloroform, alkalized with 10% sodium hydroxide and extracted with 100 ml of chloroform. The extract was washed with a saturated sodium chloride aqueous solution and dried over magnesium sulfate, and after removing the solvent under a reduced pressure the residue was subjected to silica gel chromatography with chloroform/methanol (9:1) as eluenet to obtain 1.38 g of desired compound as pale yellow liquid, from a second fraction.

$^1$H—NMR (CDCl$_3$, δ ppm): 1.95 (4H, m), 2.23 (12H, s), 2.38 (4H, t, J=7 Hz), 3.08 (4H, t, J=7 Hz), 8.05 (4H, s).

EXAMPLE 2

1,4-Bis(4-trimethylammoniobutyryl)benzene diiodide 0.28 g of 1,4-bis(4-dimethylaminobutyryl)benzene and 1.42 g of methyl iodide were dissolved in 5 ml of absolute methanol, and the solution was heated to reflux for 2 hours. After cooling to a room temperature, a resulting crystal was collected by filtration, washed with methanol and dried in vacuo to obtain 0.27 g of the title compound as a pale yellow crystal.

Melting point: 282° C. (decomposed);

$^1$H—NMR(DMSO-d6, δ ppm): 2.07 (4H, m), 3.12 (18H, s), 3.13-3.43 (8H, m), 8.13 (4H, s).

REFERENCE EXAMPLE 7

1,4-Bis(4-dimethylamino-1-hydroxybutyl)benzene

Under nitrogen flow, to 5 ml of absolute tetrahydrofuran was added 0.73 g of metallic magnesium followed by dropwise addition of 0.56 g of 1,2-dibromoethane, and on a start of reaction, a solution of 3.1 g of 3-(N,N-dimethylamimo)propyl chloride in 5 ml of absolute tetrahydrofuran was further added dropwise. The mixture was heated to reflux for 1 hour, then cooled to a room temperature, to the reaction mixture was added dropwise a solution of 1.47 g of terephtharaldehyde in absolute tetrahydrofuran. After heating to reflux for an additional one hour, chloroform was added thereto. The solvent was removed under a reduced pressure, and the residue was acidified by 6N hydrochloric acid, stirred at a room temperature for 20 minutes, and filtered. The filtrate was washed with chloroform, alkalized with 10% sodium hydroxide, salted-out with sodium chloride and extracted with 100 ml of chloroform. The extract was washed with a saturated sodium chloride aqueous solution, dried over magnesium sulfate and evaporated under a reduced pressure to obtain 2.76 g of a residue. The residue was applied with chloroform/triethylamine (10:1) to silica gel column, and from a methanol elute fraction, 0.4 g of the title compound was obtained as a colorless crystal.

$^1$H—NMR (CDCl$_3$, δ ppm): 1.55-2.06 (8H, m), 2.28 (12H, s), 2.38 (4H, m), 4.69 (2H, m), 7.35 (4H, s).

EXAMPLE 3

1,4-Bis(1-hydroxy-4-trimethylammoniobutyl)benzene diiodide

First, 0.21 g of 1,4-bis(4-dimethylamino-1-hydroxybutyl)benzene and 1.0 g of methyl iodide were dissolved in 4 ml of absolute methanol. The solution was heated to reflux for 2 hours, cooled to a room temperature, and allowed to stand in a freezer overnight. A resulting crystal was collected by filtration, washed with acetone and methanol, and dried in vacuo to obtain 0.22 g of the title compound as a pale yellow crystal.

Melting point: 243° C. (decomposed);

$^1$H—NMR(DMSO-d6, δ ppm): 1.47-1.90 (8H, m), 3.07 (18H, s), 3.25-3.43 (4H, m), 4.58 (2H, m), 5.29 (2H, d, J=4 Hz), 7.32 (4H, s).

REFERENCE EXAMPLE 8

1,4-Bis(1-acetoxy-4-dimethylaminobutyl)benzene 0.24 g of 1,4-bis(4-dimethylamino-1-hydroxybutyl)-benzene, 1.02 g of acetic anhydride and 0.08 g of pyridine were mixed to a homogeneous solution, which was then stirred at a room temperature for 7 hours. After adding chloroform, the mixture was evaporated under a reduced pressure, and after adding toluene, evaporated under a reduced pressure, alkalized by addition of 10% sodium hydroxide and extracted with 50 ml of chloroform. The extract was washed with a saturated sodium chloride aqueous solution, dried over magnesium sulfate and evaporated under a reduced pressure to obtain 0.27 g of the title compound as a pale yellow liquid.

$^1$H—NMR (CDC$_{13}$, δ ppm): 1.30–1.99 (8H, m), 2.08 (6H, s), 2.18 (12H, s), 2.20–2.32 (4H, m), 5.74 (2H, t, J=7 Hz), 7.30 (4H, s).

EXAMPLE 4

1,4-Bis(1-acetoxy-4-trimethylammoniobutyl)benzene diiodide

First, 0.24 g of 1,4-bis(1-acetoxy-4-dimethylaminobutyl)benzene and 1.42 g of methyl iodide were dissolved in 5 ml of absolute methanol, and the solution was heated to reflux for 2 hours and cooled at a room temperature. The resulting crystal was collected by filtration, washed with methanol, and dried under a reduced pressure to obtain 0.21 g of the title compound as a pale yellow crystal.

Melting point: 254° C. (decomposed);

$^1$H—NMR (DMSO-d6, δ ppm): 1.78 (8H, m), 2.10 (6H, s), 3.04 (18H, s), 3.33 (4H, m), 5.70 (2H, m), 7.39 (4H s).

REFERENCE EXAMPLE 9

1,4-Bis(3-dimethylaminopropyl)benzene

To 1.60 g of 1,4-bis(3-bromopropyl)benzene were added 2.62 ml of ethanol and then 2.62 ml of 50% dimethylamine aqueous solution, and the mixture was stirred at a room temperature overnight. The resulting colorless solution was diluted with 50 ml of benzene, washed with 5% sodium bicarbonate aqueous solution, twice with water and then with a saturated sodium chloride aqueous solution, dried over magnesium sulfate, and evaporated under a reduced pressure to obtain 960 mg of the title compound as a colorless liquid.

$^1$H—NMR (CDCl$_3$, δ ppm): 1.77 (4H, m), 2.22 (12H, s), 2.29 (4H, t, J=7.3 Hz), 2.60 (4H, t, J=7.8 Hz), 7.10 (4H, s).

EXAMPLE 5

1,4-Bis(3-trimethylammoniopropyl)benzene diiodide 248 mg of 1,4-bis(3-dimethylaminopropyl)benzene was dissolved in 2.5 ml of absolute methanol, to the mixture was added dropwise 1.42 g of methyl iodide. The mixture was kept in dark at a room temperature for 135 minutes, and heated to reflux for further one hour to obtain a pale yellow solution. The solution was allowed to be cooled, and a resulting crystal was collected by filtration, washed with methanol, and dried under a reduced pressure to obtain 358 mg of the title compound as a pale yellow crystal.

$^1$H—NMR (D20, δ ppm): 2.0–2.3 (4H, m), 2.73 (4H, t, J=7.3 Hz), 3.09 (18H, s), 3.2–3.4 (4H, m), 7.29 (4H, s); UV (max): 222 nm.

REFERENCE EXAMPLE 10

1,4-Bis(3-diethylaminopropyl)benzene

To 1.60 g of 1,4-bis(3-bromopropyl)benzene were added 3.66 ml of ethanol, 1.83 ml of water and 1.83 g of diethylamine, and the mixture was stirred for 2 hours at 80° C. to obtain a homogeneous pale brown solution. It was then diluted with 50 ml of benzene, sequentially washed with 5% sodium bicarbonate aqueous solution, twice with water and a saturated sodium chloride aqueous solution, dried over magnesium sulfate and evaporated under a reduced pressure to obtain 1.23 g of the title compound as a pale yellow liquid.

$^1$H—NMR (CDCl$_3$, δ ppm): 1.00 (12H, t, J=7.2 Hz), 1.7–1.9 (4H, m), 2.4–2.7 (16H, m), 7.10 (4H, s).

EXAMPLE 6

1,4-Bis(3-triethylammoniopropyl)benzene diiodide 304 mg of 1,4-bis(3-diethylaminopropyl)benzene was dissolved in 2.5 ml of absolute ethanol, and after dropwise addition of 1.56 g of ethyl iodide, the mixture was refluxed for 1.5 hours in dark. After cooling, ethanol was partially removed under reduced pressure, the resulting crystal was filtered, quickly washed with ethanol and dried in vacuo to obtain 461 mg of the title compound as a colorless crystal.

$^1$H—NMR (D 0, δ ppm): 1.18 (18H, brt, J=7.1 Hz), 1.9–2.1 (4H, m), 2.72 (4H, t, J=7.2 Hz), 3.1–3.3 (16H, m), 7.30 (4H, s).

EXAMPLE 7

1,4-Bis3-(1-methyl-1-piperidinio)propyl]benzene dibromide

First, 320 mg of 1,4-bis(3-bromopropyl)benzene was dissolved in 2.0 ml of ethanol, 365 μl of N-methylpiperidine was added dropwise thereto, and the mixture was refluxed for 5 hours, cooled and concentrated under a reduced pressure. After addition of acetone, the mixture was allowed to stand. The crystallizing product was filtered, washed with acetone quickly and dried under a reduced pressure to obtain 435 mg of the title compound as a colorless crystal.

$^1$H—NMR (D 0, δ ppm): 1.5–1.7 (4H, m], 1.81 (8H, brs), 2.0–2.1 (4H, m), 2.72 (4H, t, J=7.3 Hz), 2.99 (6H, s), 3.2–3.4 (12H, m), 7.29 (4H, s).

EXAMPLE 8

1,4-Bis[3-(1-pyridinio)propyl]benzene dibromide

First, 320 mg of 1,4-bis(3-bromopropyl)benzene was dissolved in 5.0 ml of ethanol, 202 μl of pyridine was added thereto, the mixture was then refluxed for 18 hours. After cooling, to the reaction mixture was added 20 ml of ethyl ether. The resulting solids were recrystallized from ethanol/ethyl ether to obtain 215 mg of the title compound as a colorless crystal.

$^1$H—NMR (DMSO-d6, δ ppm): 2.1–2.4 (4H, m), 2.5–2.7 (4H, m), 4.68 (4H, t, J=7.3 Hz), 7.13 (4H, s), 8.16 (4H, dd; J=5.4, 7.8 Hz), 8.61 (2H, t, J=7.8 Hz), 9.14 (4H, d, J=5.4 Hz).

REFERENCE EXAMPLE 11

1,4-Bis(4,4-diethoxycarbonylbutyl)benzene

First, to 483 mg of metallic sodium dissolved in 21 ml of absolute ethanol, 6.72 g of diethyl malonate was added dropwise, and the mixture was refluxed for 5 minutes. After cooling, to the solution was added dropwise a mixture of 3.2 g of 1,4-bis(3-bromopropyl)benzene and diethyl malonate over 5 minutes, and the mixture was refluxed for 40 minutes to obtain a white suspension. After cooling and addition of 21 ml of ice water, the mixture was adjusted to pH 7.0 with 1N hydrochloric acid, and ethanol was removed under a reduced pressure to obtain an aqueous layer, which was then twice extracted with 100 ml of benzene each time. The extract was washed with a saturated sodium chloride aqueous solution, dried over magnesium sulfate and evaporated under a reduced pressure to remove the solvent, and then to remove any unreacted diethyl malonate under a reduced pressure at 140° C. to obtain 4.74 g of the title compound as a colorless liquid.

$^1$H—NMR (CDCl$_3$, δ ppm): 1.25 (12H, t, J=7.1 Hz), 1.5-1.7 (4H, m), 1.8-2.0 (4H, m), 2.60 (4H, t, J=7.7 Hz), 3.33 (2H, t, J=7.4 Hz), 4.18 (8H, q, J=7.1 Hz), 7.07 (4H, s).

REFERENCE EXAMPLE 12

1,4-Bis(5-hydroxypentyl)benzene

To 3.35 g of 1,4-bis(4,4-diethoxycarbonylbutyl)benzene were added 20 ml of acetic acid and 20 ml of concentrated hydrochloric acid, and the mixture was refluxed for 19 hours and cooled. The crystallizing-out product was filtered, washed with water and dried in vacue. To 1.70 g of the colorless crystal thus obtained were added 12 ml of ethanol and 0.61 ml of concentrated sulfuric acid, and the mixture was refluxed for 405 minutes. After cooling the reaction mixture was poured on ice water, the mixture was adjusted to pH 7.0 with 10% sodium hydroxide, and evaporated under a reduced pressure to remove the ethanol solvent, then extracted with 100 ml of ethyl acetate. The extract was washed with a saturated sodium chloride aqueous solution, dried over magnesium sulfate, and evaporated under reduced pressure to obtain 2.01 g of a pale yellow liquid.

$^1$H—NMR (CDCl$_3$, δ ppm): 1.24 (6H, t, J=7.1 Hz), 1.5-1.8 (8H, m), 2.31 (4H, brt), 2.59 (4H, brt), 4.12 (4H, q, J=7.1 Hz), 7.08 (4H, s).

Next, 2.0 g of the pale yellow liquid thus obtained was dissolved in 10 ml of absolute tetrahydrofuran, to the solution was added dropwise a suspension of 342 mg of lithium aluminum hydride in 24 ml of absolute tetrahydrofuran at 50 to 60° C. with stirring. The mixture was refluxed for one hour, then ice cooled, and after dropwise adding successively 0.5 ml of water, 0.5 ml of 15% sodium hydroxide and 1.5 ml of water, the mixture was stirred at a room temperature for one hour. Resulting insoluble matter was filtered off, and the solvent was removed under reduced pressure to obtain 1.47 g of the title compound as a colorless crystalline powder.

$^1$H—NMR (CDCl$_3$, δ ppm): 1.3-1.7 (14H, m), 2.59 (4H, t, J=7.6 Hz), 3.63 (4H, t, J=6.5 Hz), 7.08 (4H, s).

REFERENCE EXAMPLE 13

1,4-Bis(5-bromopentyl)benzene

To 1.45 g of 1,4-bis(5-hydroxypentyl)benzene was added 451 µl of phosphorous tribromide under ice cooling, and the mixture was stirred at 80° C. for one hour. After cooling and adding ice water, the mixture was extracted with 100 ml of ethyl acetate, and the extract was successively washed with a 5% sodium bicarbonate aqueous solution, water and a saturated sodium chloride aqueous solution, dried over magnesium sulfate, and evaporated to remove the solvent under a reduced pressure. The residue was purified by silica gel column chromatography using benzene/hexane (5:1) as eluent to obtain 1.70 g of the title compound as a colorless liquid.

$^1$H—NMR (CDCl$_3$, δ ppm): 1.4-1.8 (8H, m), 1.8-2.0 (4H, m), 2.59 (4H, brt), 3.40 (4H, t, J=6.8 Hz), 7.09 (4H, s).

REFERENCE EXAMPLE 14

1,4-Bis(5-dimethylaminopentyl)benzene

To a solution of 376 mg of 1,4-bis(5-bromopentyl)benzene dissolved in 0.5 ml of ethanol, 523 µl of 50% dimethylamine aqueous solution was added, and the mixture was stirred at a room temperature overnight. After the reaction was completed, to the reaction mixture were added 10 ml of benzene and 5 ml of 5% sodium bicarbonate aqueous solution, and separated. The organic layer was successively washed with water and a saturated sodium chloride aqueous solution, dried over magnesium sulfate, and evaporated under reduced pressure. The residue was allowed to stand overnight to obtain 248 mg of colorless crystal.

$^1$H—NMR (CDCl$_3$, δ ppm): 1.3-1.7 (12H, m), 2.22 (12H, s), 2.2-2.3 (4H, m), 2.58 (4H, t, J=7.7 Hz), 7.08 (4H, s).

EXAMPLE 9

1,4-Bis(5-trimethylammoniopentyl)benzene diiodide

To a solution of 237 mg of 1,4-bis(5-dimethylaminopentyl)benzene in 2 ml of absolute methanol, 486 µl of methyl iodide was added, and then the mixture was stirred at a room temperature for 5 hours and concentrated. To the concentrate was added acetone to form crystal. It was filtered, washed with acetone and dried under a reduced pressure to obtain 422 mg of the title compound as a colorless crystal.

$^1$H—NMR (D 0, δ ppm): 1.3-1.5 (4H, m), 1.5-1.9 (8H, m), 2.63 (4H, brt), 3.08 (18H, s), 3.2-3.3 (4H, m), 7.23 (4H, s).

REFERENCE EXAMPLE 15

1,4-Bis(5-diethylaminopentyl)benzene

To 376 mg of 1,4-bis(5-bromopentyl)benzene were added 1.0 ml of ethanol and 0.5 ml of water and then 516 µl of diethylamine, and the mixture was refluxed for 2 hours. To the reaction mixture were added 15 ml of ethyl acetate and 5 ml of 5% sodium bicarbonate aqueous solution, and separated. The organic layer was washed with water and a saturated sodium chloride aqueous solution, dried over magnesium sulfate, and evaporated under reduced pressure to obtain 312 mg of the title compound as a pale yellow liquid.

$^1$H—NMR (CDCl$_3$, δ ppm): 1.02 (12H, t, J=7.2 Hz), 1.1-1.8 (12H, m), 2.3-2.7 (16H, m), 7.08 (4H, s).

EXAMPLE 10

1,4-Bis(5-triethylammoniopentyl)benzene diiodide

To a solution of 312 mg of 1,4-bis(5-diethylaminopentyl)benzene in 2 ml of absolute ethanol, 696 µl of ethyl iodide was added. The mixture was refluxed for 3 hours, and after cooling, evaporated to remove the ethanol. The pale yellow oil residue was diluted with 1 ml of acetone and stirred with 0.5 ml of ethyl acetate. The crystallizing product was filtered, successively washed with acetone and hexane, and dried under a reduced pressure to obtain 450 mg of the title compound as a yellow crystal.

$^1$H—NMR (D$_2$O, δ ppm): 1.23 (18H, brt), 1.3–1.5 (4H, m), 1.5–1.8 (8H, m), 2.63 (4H, brt), 3.0–3.2 (4H, m), 3.24 (12H, q, J=7.1 Hz), 7.23 (4H, s).

EXAMPLE 11

1,4-Bis[4-(1-methyl-1-piperidinio)pentylbenzene dibromide

To a solution of 376 mg of 1,4-bis(5-bromopentyl)-benzene in 2 ml of absolute ethanol, 365 μl of N-methylpyridine was added, and the mixture was refluxed for 5 hours. After concentration under a reduced pressure and addition of acetone, and the mixture was allowed to stand overnight. The product was filtered and recrystallized from ethanol (0.5 ml)—acetone (2 ml) to obtain 455 mg of the title compound as a colorless crystal.

$^1$H—NMR (D$_2$O, δ ppm): 1.3–1.5 (4H, m), 1.5–2.0 (20H, m), 2.63 (4H, t, J=7.5 Hz), 2.99 (6H, s), 3.2–3.4 (12H, m), 7.23 (4H, s).

REFERENCE EXAMPLE 16

1,4-Bis(2-chloroethoxymethyl)benzene

To 5.0 g of p-xylylene dichloride was added 25 ml of 2-chloroethanol, and the mixture was refluxed for 24 hours. After the reaction, 2-chloroethanol was removed under reduce pressure at 100° C. The residue was applied to a silica gel column and eluted with hexane/chloroform (1:1) as eluent, and a relevant fraction was further purified by distillation to obtain 2.44 g of the title compound as a colorless liquid.

1H—MR (CDCl$_3$, δ ppm): 3.6–3.8 (8H, m), 4.59 (4H, s), 7.34 (4H, s).

REFERENCE EXAMPLE 17

1,4-Bis(2-dimethylaminoethoxymethyl)benzene

To 240 mg of 1,4-bis(2-chloroethoxymethyl)benzene were added 477 μl of 50% dimethylamine aqueous solution and 0.5 ml of ethanol, and the mixture was heated in a sealed tube at 100° C. for 3.5 hours. To the reaction mixture were added 20 ml of ethyl acetate and 5 ml of 5% sodium bicarbonate aqueous solution. The ethyl acetate layer was separated, washed with a saturated sodium chloride aqueous solution, dried over magnesium sulfate and evaporated under reduce pressure to obtain 205 mg of the title compound as a colorless liquid.

$^1$H—NMR (CDCl$_3$, δ ppm): 2.26 (12H, s), 2.53 (4H, t, J=5.8 Hz), 3.54 (4H, t, J=5.8 Hz), 4.53 (4H, s), 7.32 (4H, s).

EXAMPLE 12

1,4-Bis(2-trimethylammonioethoxymethyl)benzene diiodide

To a solution of 200 mg of 1,4-bis(2-dimethylaminoethoxymethyl)benzene in 2 ml of absolute methanol, 598 μl of methyl iodide was added with stirring at a room temperature, and after forming insoluble matter, the mixture was refluxed for one hour. After cooling, the insoluble matter was filtered, washed with methanol and dried under a reduced pressure to obtain 335 mg of the title compound as a pale yellow crystal.

$^1$H—NMR (D$_2$O, δ ppm): 3.18 (18H, s), 3.62 (4H, brt), 3.1–4.1 (4H, m), 4.65 (4H, s), 7.47 (4H, s).

REFERENCE EXAMPLE 18

1,4-Bis[4,4-bis(hydroxymethyl)butyl]benzene

First, 525 mg of lithium aluminium hydride was added to 30 ml of absolute tetrahydrofuran, then 20 ml of a solution of 2.39 g 1,4-bis(4,4-diethoxycarbonyl-butyl)benzene in absolute tetrahydrofuran was added dropwise thereto with stirring at a room temperature, and the mixture was refluxed for one hour. After adding 4 ml of ethyl acetate with ice-cooling, the reaction mixture was stirred for 10 minutes. To the mixture were further added successively 0.5 ml of water, 0.5 ml of 15% sodium hydroxide aqueous solution and 1.5 ml of water, and the mixture was stirred for one hour. After filtering off insoluble matter, the filtrate was evaporated under a reduced pressure. The oily residue thus obtained was applied to a silica gel column and eluted with chloroform/ethanol (5:1) to obtain 350 mg of the title compound as a colorless crystal.

EI Mass m/z: 310 (M$^{30}$);

$^1$H—NMR (DMSO-d6, δ ppm): 1.2–1.4 (4H, s), 1.4–1.7 (6H, m), 2.50 (4H, brt), 3.3–3.4 (8H, m), 4.26 (4H, t, J=5.1 Hz), 7.07 (4H, s).

REFERENCE EXAMPLE 19

1,4-Bis4,4-bis(bromomethyl)butyl]benzene

To 337 mg of 1,4-bis[4,4-bis(hydroxymethyl)butyl]-benzene was added 168 μl of phosphorus tribromide, and after the mixture was stirred at 80° C. for 75 minutes, 20 ml of ethyl acetate and 10 ml of ice water were added. The separated organic layer was, washed with water, 5% sodium bicarbonate aqueous solution and a saturated sodium chloride aqueous solution, dried over magnesium sulfate, and evaporated under a reduced pressure. The oily residue was applied to a silica gel column and eluted with benzene/hexane (1:9) to obtain 151 mg of the title compound as a colorless liquid.

EI Mass m/z: 558 (M+);

$^1$H—NMR (CDC$_{13}$, δ ppm): 1.4–1.8 (8H, m), 1.9–2.1 (2H, m), 2.06 (4H, t, J=7.5 Hz), 3.47 (4H, dd, J=6.1, 10.3 Hz), 3.59 (4H, dd, J=4.2, 10.3 Hz), 7.09 (4H, s).

REFERENCE EXAMPLE 20

1,4-Bis4,4-bis(dimethylaminomethyl)butyl]benzene

To 150 mg of 1,4-bis[4,4-bis(bromomethyl)butyl]benzene in a flask were added 283 μl of 50% dimethylamine and 0.5 ml of ethanol, and the flask was provided with a gum balloon at the top. The mixture in the flask was stirred at 70° C. for one hour, and to the reaction mixture were added 20 ml of ethyl acetate and 5 ml of 5% sodium bicarbonate aqueous solution. The separated organic layer was washed with a saturated sodium chloride aqueous solution, dried over magnesium sulfate and evaporated under a reduced pressure to obtain 72 mg of the title compound as a pale yellow liquid.

EI Mass m/z: 418 (M+);

$^1$H—NMR (CDC$_{13}$, δ ppm): 1.3–1.5 (4H, m), 1.5–1.8 (6H, m), 2.1–2.3 (8H, m), 2.19 (18H, s), 2.57 (4H, brt), 7.09 (4H, s).

EXAMPLE 13

1,4-Bis4,4-bis(trimethylammoniomethyl)butyl]benzene tetraiodide

To a solution of 73 mg of 1,4-bis[4,4-bis(dimethylaminomethyl)butyl]benzene in 1 ml of methanol, 318 μl of methyl iodide was added, and the mixture was refluxed for one hour and then cooled. The crystallizing product was filtered, washed with methanol and acetone, and dried under a reduced pressure to obtain 107 mg of the title compound as a yellow crystal.

$^1$H—NMR (D20, δ ppm): 1.76 (8H, brs), 2.5-2.8 (6H, m), 3.19 (36H, s), 3.3-3.6 (8H, m), 7.26 (4H, s).

REFERENCE EXAMPLE 21

Ethyl 4-phenylbutylate

To a solution of 16.4 g of 4-phenylbutylic acid in 200 ml of ethanol, 10 ml of concentrated sulfuric acid was added dropwise at a room temperature with stirring, and the reaction mixture was refluxed for 4 hours. The reaction mixture was poured on 200 ml of ice water, adjusted to pH 7.5 with 10% sodium hydroxide, and evaporated under a reduced pressure to remove the ethanol. The residual solution was extracted with 300 ml of ethyl acetate, and the extract was successively washed three times with water and once with a saturated sodium chloride aqueous solution, dried over magnesium sulfate, and evaporated under a reduced pressure to obtain 18.5 g of the title compound as a colorless liquid.

$^1$H—NMR (CDCl$_3$, δ ppm): 1.25 (3H, t, J=7.1 Hz), 1.9-2.1 (2H, m), 2.32 (2H, t, J=7.6 Hz), 2.65 (2H, t, J=7.5 Hz), 4.12 (2H, q, J=7.1 Hz), 7.1-7.4 (5H, m).

REFERENCE EXAMPLE 22

4-Phenylbutanol

To a suspension of 266 mg of lithium aluminium hydride in 10 ml of absolute tetrahydrofuran, a solution of 1.92 g ethyl 4-phenylbutylate in 10 ml of absolute tetrahydrofuran was added dropwise at a temperature of 50° to 60° C. over 10 minutes, and the mixture, was then refluxed for one hour. After ice cooling, 0.27 ml of water, 0.27 ml of 15% sodium hydroxide solution and 0.81 ml of water were successively added with stirring. The reaction mixture was stirred at a room temperature for one hour, filtered to remove the insoluble matter, and evaporated to obtain 1.49 g of the title compound as a colorless liquid.

$^1$H—NMR (CDCl$_3$, δ ppm): 1.30 ($^1$H, brs), 1.5-1.8 (4H, m), 2.65 (2H, t, J=7.3 Hz), 3.65 (2H, t, J=6.1 Hz), 7.1-7.4 (5H, m).

REFERENCE EXAMPLE 23

N,N-dimethyl-4-phenylbutylamine

To 1.50 g of 4-phenylbutanol was added 385 μl of phosphorus tribromide with ice cooling, and the mixture was stirred at a room temperature for 5 minutes and then at 80° C. for one hour. To the reaction mixture were added 20 ml of ice water and 30 ml of ethyl acetate. The separated organic layer was, successively washed with water, 5% sodium bicarbonate aqueous solution and a saturated sodium chloride aqueous solution, dried over magnesium sulfate, and evaporated under a reduced pressure to obtain an oily residue. The residue was applied to a silica gel column and eluted with hexane/benzene (6:1) to obtain 1.94 g of (4-bromobutyl)benzene as a colorless liquid.

To 426 mg of the colorless liquid (4-bromobutyl)benzene were added 1.05 ml of 50% dimethylamine aqueous solution and 1 ml of ethanol, and the mixture was stirred at a room temperature for 520 minutes. To the reaction mixture were added 30 ml of ethyl acetate and 10 ml of 5% sodium bicarbonate aqueous solution. The separated organic layer was washed with a saturated sodium chloride aqueous solution, dried over magnesium sulfate, and evaporated under a reduced pressure to obtain a residue. To the residue was added 20 ml of benzene, then was washed with water and a saturated sodium chloride aqueous solution, dried over magnesium sulfate, and evaporated under a reduced pressure to obtain 287 mg of the title compound as colorless liquid.

$^1$H—NMR (CDCl$_3$, δ ppm): 1.2-1.7 (4H, m), 2.20 (6H, s), 2.26 (2H, t, J=7.3 Hz), 2.63 (2H, t, J=7.4 Hz), 7.1-7.3 (5H, m).

REFERENCE EXAMPLE 24

N,N,N-Trimethyl-4-phenylbutylammonium iodide

To a solution of 287 mg of N,N-dimethyl-4-phenylbutylamine in 3 ml of absolute methanol, 505 μl of methyl iodide was added at a room temperature with stirring, and the mixture was stirred at a room temperature for 6.5 hours. The reaction mixture was concentrated under a reduced pressure, and after adding ethyl acetate allowed to stand for formation of crystal. The crystal was filtered, washed with ethyl acetate, and dried under a reduced pressure to obtain 439 mg of the title compound as a colorless crystal.

$^1$H—NMR (D$_2$O, δ ppm): 1.6-1.9 (4H, m), 2.71 (2H, brt), 3.05 (9H, s), 3.30 (2H, brt), 7.2-7.5 (5H, brs).

REFERENCE EXAMPLE 25

4-Phenylbutylaldehyde

First, 3.84 g of ethyl 4-phenylbutylate was dissolved in 40 ml of absolute n-hexane, and after cooling with dry ice/acetone, 28 ml of 1M diisobutylaluminium hydride in n-hexane was added dropwise to the mixture at −60° C. with stirring over 15 minutes, and the mixture was stirred at the same temperature for 70 minutes. Moreover, at the same temperature 3 ml of ethanol/3 ml of n-hexane, 3.6 ml of ethanol, and 3.3 ml of water/6.6 ml of ethanol were successively added dropwise to the reaction mixture, which was then allowed to warm to a room temperature by removing a cooling bath. The reaction mixture was adjusted to pH 3.0 with 1N and 6N hydrochloric acid to dissolve most of the insoluble matter. 100 ml of n-hexane was added to the reaction mixture and layers were separated. The n-hexane layer was washed with water and a saturated sodium chloride aqueous solution, dried over magnesium sulfate, and evaporated under a reduced pressure to obtain a colorless oil. The oil was applied to a silica gel column and eluted with hexane/ethyl acetate (20:1) to obtain 2.11 g of title compound as a colorless liquid.

$^1$H—NMR (CDC$_{13}$, δ ppm): 1.9-2.1 (2H, m), 2.45 (2H, d, t, J=1.5, 7.4 Hz), 2.66 (2H, t, J=7.4 Hz), 7.1-7.4 (5H, m), 9.75 ($^1$H, t, J=1.5 Hz).

REFERENCE EXAMPLE 26

Ethyl 8-phenyl-4-octenoate

First, 207 mg of metalic sodium was dissolved in 4 ml of absolute ethanol, and the ethanol was evaporated off to obtain sodium ethoxide powder, to which was then added at once a solution of 4.75 g ethoxycarbonylpropyltriphenylphosphonium bromide in 15 ml of absolute dimethylformamide with stirring. The mixture was stirred for 1.5 hours, and after adding dropwise a solution of 1.04 g 4-phenylbutylaldehyde in 5 ml of absolute dimethylformamide at 5° C. over 5 minutes, stirred overnight at a room temperature. To the reaction mixture were added 100 ml of n-hexane and 30 ml of water and the resulting layers were separated, and the aqueous solution was extracted with 20 ml of n-hexane. The n-hexane layers were combined, washed with water and a saturated sodium chloride aqueous solution, dried over magnesium sulfate and evaporated under a reduced pressure to obtain an oily residue. The residue was applied to a silica gel column and eluted with n-hexane/ethyl acetate (50:1) to obtain 831 mg of the title compound as a colorless liquid.

$^1$H—NMR (CDCl$_3$, δ ppm): 1.25 (3H, t, J=7.1 Hz), 1.6–1.8 (2H, m), 2.0–2.2 (2H, m), 2.33 (4H, brs), 2.62 (2H, t, J=7.8 Hz), 4.12 (2H, t, J=7.1 Hz), 5.3–5.5 (2H, m), 7.1–7.4 (5H, m).

REFERENCE EXAMPLE 27

8-Phenyloctanol

First, 831 mg of et - 8-phenyl-4-octenoate was dissolved in 17 ml of absolute ethanol, and after adding 83 mg of 5% palladium on carbon, the mixture was stirred under a hydrogen gas flow at a room temperature for 80 minutes. After filtering off the catalyst, the filtrate was evaporated to obtain 795 mg of ethyl 8-phenyloctanoate as a colorless liquid.

$^1$H—NMR (CDCl$_3$, δ ppm): 1.25 (3H, t, J=7.1 Hz), 1.32 (6H, brs), 1.5–1.7 (4H, m), 2.28 (2H, t, J=7.4 Hz), 2.60 (2H, t, J=7.7 Hz), 4.12 (2H, t, J=7.1 Hz), 7.1–7.4 (5H, m).

Next, 795 mg of the liquid thus obtained was dissolved in 5 ml of absolute tetrahydrofuran, and after adding dropwise a suspension of 122 mg lithium aluminium hydride in 5 ml of absolute tetrahydrofuran with stirring at a room temperature, the mixture was stirred at the same temperature for 160 minutes. The reaction mixture was ice-cooled, and after adding successively dropwise 122 μl of water, 122 μl of 15% sodium hydroxide aqueous solution and 365 μl of water, stirred for 100 minutes, filtered to remove the insoluble matter and evaporated under a reduced pressure to obtain 825 mg of crude 8-phenyloctanol as a colorless oil.

REFERENCE EXAMPLE 28

(8-Bromooctyl)benzene

To 825 mg of the obtained in Reference Example 27, were added 154 μl of phosphorus tribromide with ice-cooling, and the mixture was heated to 80° C. for an hour with stirring. To the mixture were added 30 ml of ethyl acetate and 10 ml of ice water. The separated organic layer was, washed with water, 5% sodium bicarbonate aqueous solution and a saturated sodium chloride aqueous solution, dried over magnesium sulfate, and evaporated under a reduced pressure. The resulting oily residue was applied to a silica gel column, and eluted with hexane to obtain 681 mg of the title compound as a colorless liquid.

$^1$H—NMR (CDC$_{13}$, δ ppm): 1.34 (8H, brs), 1.5–1.7 (2H, m), 1.8–2.0 (2H, m), 2.61 (2H, t, J=7.7 Hz), 3.41 (2H, t, J=6.8 Hz), 7.1–7.4 (5H, m).

REFERENCE EXAMPLE 29

N,N-Dimethyl-8-phenyloctylamine

To 538 mg of (8-bromooctyl)benzene were added 1 ml of ethanol and 1.05 ml of 50% aqueous diethylamine solution, and the mixture was stirred at a room temperature for 7.5 hours. To the mixture were added 30 ml of ethyl acetate and 5 ml of 5% sodium bicarbonate aqueous solution, and the resulting layers were separated. The organic layer was washed with water and a saturated sodium chloride aqueous solution, dried over magnesium sulfate, and evaporated under a reduced pressure. The residue was applied to a silica gel column and eluted with chloroform/methanol (9:1) to eliminate impurities appeared on the start point on thin layer chromatography. In this way, compound as colorless liquid, 378 mg of the title compound was obtained as colorless liquid.

$^1$H—NMR (CDCl$_3$, δ ppm): 1.31 (8H, brs), 1.3–1.5 (2H, m), 1.5–1.7 (2H, m), 2.21 (6H, s), 2.23 (2H, t, J=7.3 Hz), 2.60 (2H, t, J=7.7 Hz), 7.1–7.4 (5H, m).

EXAMPLE 14

N,N,N-Trimethyl-8-phenyloctylammonium iodide

To a solution of 193 mg of N,N-dimethyl-8-phenyloctylamine in 1.5 ml of absolute methanol, were added dropwise 258 μl of methyl iodide, and the mixture was stirred at a room temperature for 6.5 hours. After adding 3 ml of ethyl acetate, the mixture was stirred with ice-cooling for 30 minutes. Resulting crystal was filtered, washed with ethyl acetate, and dried under a reduced pressure to obtain 238 mg of the title compound as a colorless crystal.

$^1$H—NMR (DMSO-d6, & ppm): 1.30 (8H, brs), 1.5–1.8 (4H, m), 2.75 (2H, brt), 3.03 (9H, s), 3.2–3.4 (2H, m), 7.1–7.4 (5H, m).

EXAMPLE 15

N,N,N-Trimethyl-8-phenyloctylammonium p-tosylate

To a solution of 184 mg of N,N-dimethyl-8-phenyloctylamine in 1.58 ml of absolute methanol, 368 mg of methyl tosylate was added at room temperature, the mixture was stirred for 4 hours and concentrated. The resulting crystal was filtered, washed with ethyl acetate and dried under a reduced pressure to obtain 315 mg of the title compound as a colorless crystal.

$^1$H—NMR (D20, δ ppm): 0.9–1.3 (8H, m), 1.3–1.6 (4H, m), 2.19 (3H, s), 2.52 (2H, brt), 3.04 (11H, brs), 7.0–7.1 (7H, m), 7.74 (2H, d, J=8.1 Hz).

REFERENCE EXAMPLE 30

1,3-Bis[4-(2-tetrahydropyranyloxy)butyl]benzene

To 17.5 ml of absolute n-hexane were added dropwise 530 mg of m-xylene and 1.40 g of potassium t-butoxide, followed by addition of 8.4 ml of 1.6M solution of n-butyl lithium in n-hexane over 5 minutes with stirring at a room temperature, and the mixture was refluxed for an hour to obtain a orange suspension. This reaction mixture was cooled with dry ice/acetone, and after adding at once a solution of 3.35 g 2-(3-bromopropyloxy)tetrahydropyran in absolute n-hexane with stirring, further stirred for 5 minutes, warmed to a room temperature and stirred at the same temperature overnight. To a pale yellow suspension thus obtained were added 20 ml of ice water and 50 ml of n-hexane. The separated organic layer was washed with water and a saturated sodium chloride aqueous solution, dried over magnesium sulfate, and evaporated under a reduced pressure to remove the solvent. The resulting oily residue was applied to a silica gel column and eluted with hexane/ethyl acetate (20:1) to obtain 913 mg of the title compound as a colorless liquid.

$^1$H—NMR (CDCl$_3$, δ ppm): 1.4–1.9 (20H, m), 2.61 (4H, brt), 3.3–3.6 (4H, m), 3.7–4.0 (4H, m), 4.57 (2H, brt), 6.9–7.2 (4H, m).

REFERENCE EXAMPLE 31

1,3-Bis(4-hydroxybutyl)benzene

To a solution of, 822 mg of 1,3-bis[4-(2-tetrahydropyranyloxy)butyl]benzene in 3 ml of ethanol was added 1.5 ml of 6N hydrochloric acid, and after stirring at a room temperature for 7 hours, 30 ml of ethyl acetate and 10 ml of ice water were added. The separated organic layer was washed with 5% sodium bicarbonate aqueous solution, water and a saturated sodium chloride, dried over magnesium sulfate, and evaporated under a reduced pressure to remove the solvent. The resulting oily residue was applied to a silica gel column and eluted with chloroform/methanol (100:1) to obtain 264 mg of the title compound as a colorless liquid.

$^1$H—NMR (CDCl$_3$, δ ppm): 1.47 (2H, brs), 1.5–1.8 (8H, m), 2.62 (4H, t, J=7.2 Hz), 3.65 (4H, t, J=6.4 Hz), 6.9–7.2 (4H, m).

REFERENCE EXAMPLE 32

1,3-Bis(4-bromobutyl)benzene

To 264 mg of 1,3-bis(4-hydroxybutyl)benzene was added 92 μl of phosphorus tribromide under ice-cooling, and the mixture was stirred at 80° C. for an hour and after adding ice water, extracted with 50 ml of ethyl acetate. The extract was washed with 5% sodium bicarbonate aqueous solution, water and a saturated sodium chloride aqueous solution, dried over magnesium sulfate, and evaporated under a reduced pressure. The oily residue was applied to a silica gel column and eluted with hexane/benzene (10:1) to obtain 288 mg of the title compound as a colorless liquid.

$^1$H—NMR (CDCl$_3$, δ ppm): 1.7–2.0 (8H, m), 2.62 (4H, t, J=7.3 Hz), 3.42 (4H, t, J=6.5 Hz), 6.9–7.2 (4H, m).

REFERENCE EXAMPLE 33

1,3-Bis(4-dimethylaminobutyl)benzene

To 288 mg of 1,3-bis(4-bromobutyl)benzene were added 0.7 ml of ethanol and 695 μl of 50% dimethylamine aqueous solution, and the mixture was stirred at a room temperature overnight. To the reaction mixture were added 30 ml of ethyl acetate and 10 ml of 5% sodium bicarbonate aqueous solution. The separated organic layer was washed with water and a saturated sodium chloride aqueous solution, dried over magnesium sulfate, and evaporated under a reduced pressure to obtain 187 mg of the title compound as pale yellow liquid.

$^1$H—NMR (CDCl$_3$, δ ppm): 1.4–1.7 (8H, m), 2.21 (12H, s), 2.27 (4H, brt), 2.59 (4H, t, J=7.5 Hz), 6.9–7.2 (4H, m).

EXAMPLE 16

1,3-Bis(4-trimethylammoniobutyl)benzene diiodide

First, 187 mg of 1,3-bis(4-dimethylaminobutyl)benzene was dissolved in 2 ml of absolute methanol, and after adding 422 μl of methyl iodide, the mixture was stirred at a room temperature for 4 hours, and concentrated. After adding 1 ml of acetone, the resulting crystal was filtered, washed with acetone and dried under a reduced pressure to obtain 348 mg of the title compound as a colorless crystal.

$^1$H—NMR (D 0, δ ppm): 1.6–1.9 (8H, m), 2.70 (4H, brt), 3.08 (18H, s), 3.33 (4H, brt), 7.1–7.4 (4H, m).

REFERENCE EXAMPLE 34

1,2-Bis(4-hydroxybutyl)benzene

To 17.5 ml of absolute n-hexane were added 530 mg of o-xylene and 1.40 g of potassium tert.-butoxide, followed by dropwise addition of 8.4 ml of 1.6M n-butyl lithium in n-hexane over 5 minutes with stirring at a room temperature, and the mixture was refluxed for an hour to obtain a vermilion-colored suspension. The suspension was cooled with dry ice/acetone, and after adding at once solution of 4.46 g 2-(3-bromopropyloxy)-tetrahydropyran in 2.5 ml of absolute n-hexane with stirring, further stirred for 5 minutes, warmed to a room temperature, and stirred overnight. To a yellow suspension thus obtained were added 20 ml of ice water and 50 ml of n-hexane. The organic layer was separated, washed with water and a saturated sodium chloride aqueous solution, dried over magnesium sulfate, and evaporated under a reduced pressure. The resulting oily residue was applied to a silica gel column, and eluted with hexane/ethyl acetate (20:1) to obtain 747 mg of crude 1,2-bis[4-(2-tetrahydropyranyloxy)butyl]benzene as a colorless liquid.

To a solution of 747 mg of the crude product in 3 ml of ethanol 1.5 ml of 6N hydrochloric acid was added with stirring, and the mixture was stirred for further 7 hours. To the mixture were added 30 ml of ethyl acetate and 10 ml of ice water. The organic layer was separated, washed with 5% sodium bicarbonate aqueous solution, water and a saturated sodium chloride aqueous solution, dried over magnesium sulfate, and evaporated under a reduced pressure to remove the solvent. The resulting residue was applied to a silica gel column, and eluted with chloroform/methanol (100:1) to obtain 174 mg of the title compound as a colorless liquid.

$^1$H—NMR (CDCl$_3$, δ ppm): 1.5–1.8 (10H, m), 2.65 (4H, brt), 3.68 (4H, brt), 7.13 (4H, brs).

REFERENCE EXAMPLE 35

1,2-Bis(4-bromobutyl)benzene

To 174 mg of 1,2-bis(4-hydroxybutyl)benzene was added 60 μl of phosphorus tribromide with ice-cooling, the mixture was stirred at 80° C. for an hour and then cooled, and after adding 10 ml of ice water, extracted with 50 ml of ethyl acetate. The extract was successively washed with 5% sodium bicarbonate aqueous solution, water and a saturated sodium chloride aqueous solution, dried over magnesium sulfate, and evaporated under a reduced pressure. The residue was applied to a silica gel column and eluted with hexane/benzene (10:1) to obtain 189 mg of the title compound as a colorless liquid.

$^1$H—NMR (CDCl$_3$, δ ppm): 1.6–2.0 (8H, m), 2.64 (4H, brt), 3.45 (4H, t, J=6.6 Hz), 7.14 (4H, s).

REFERENCE EXAMPLE 36

1,2-Bis(4-dimethylaminobutyl)benzene

To 189 mg of 1,2-bis(4-bromobutyl)benzene were added 1.1 ml of ethanol and 565 μl of 50% aqueous dimethylamine solution, and the mixture was stirred at a room temperature overnight. To the reaction mixture were added 30 ml of ethyl acetate and 10 ml of 5% sodium bicarbonate aqueous solution. The organic layer was separated, washed with water and a saturated sodium chloride aqueous solution, dried over magnesium sulfate, and evaporated under a reduced pressure to obtain 125 mg of the title compound as a colorless liquid.

$^1$H—NMR (CDC$_{13}$, δ ppm): 1.5–1.7 (8H, m), 2.22 (12H, s), 2,28 (4H, brt), 2.62 (4H, brt), 7.12 (4H, brs).

EXAMPLE 17

1,2-Bis(4-trimethylammoniobutyl)benzene diiodide

First, 125 mg of 1,2-bis(4-dimethylaminobutyl)benzene was dissolved in 1.5 ml of absolute methanol, and after adding 280 μl of methyl iodide, the mixture was stirred at a room temperature for 3.5 hours, and concentrated under a reduced pressure. After adding 0.75 ml of acetone, the mixture was allowed to stand. The resulting crystal was filtered, washed with acetone and dried under a reduced pressure to obtain 217 mg of the title compound as a colorless crystal.

$^1$H—NMR (D20, δ ppm): 1.5–2.0 (8H, m), 2.76 (4H, brt), 3.10 (18H, s), 3.3–3.4 (4H, m), 7.2–7.4 (4H, m).

REFERENCE EXAMPLE 37

1,4-Bis(4-diethylaminobutyl)benzene

First, 1.05 g of 1,4-bis(4-bromobutyl)benzene and 1.1 g of diethylamine were dissolved in absolute ethanol, and the mixture was refluxed for an hour and then evaporated under a reduced pressure to remove the solvent. After adding chloroform, the mixture was evaporated under a reduced pressure. After adding ethyl acetate the mixture was extracted with 15 ml of 1N hydrochloric acid. The aqueous extract was alkalized with 10% sodium hydroxide, and extracted with total 70 ml of chloroform. The organic extract was washed with water and a saturated sodium chloride aqueous solution, dried over magnesium sulfate, and evaporated under a reduced pressure to obtain 0.70 g of the title compound as a colorless liquid.

$^1$H—NMR (CDCl$_3$, δ ppm): 1.01 (12H, t, J=7 Hz), 1.35–1.69 (8H, m), 2.30–2.65 (16H, m), 7.09 (4H, s).

EXAMPLE 18

1,4-Bis(triethylammoniobutyl)benzene diiodide

First, 0.56 g of 1,4-bis(diethylaminobutyl)benzene and 2.1 g of ethyl iodide were dissolved in 7 ml of absolute ethanol, and the mixture was refluxed for 4 hours. After removing the solvent under a reduced pressure and adding acetone and a small amount of ethanol, the mixture was stirred at a room temperature for 30 minutes. The resulting crystal was filtered, washed with acetone, and dried under a reduced pressure to obtain 0.335 g of the title compound as a pale yellow crystal.

Melting point: 221° C.

$^1$H—NMR (D$_2$O, δ ppm): 1.01–1.42 (8H, m), 1.50–1.85 (8H, m), 2.56–2.79 (4H, m), 2.96–3.45 (16H, m), 7.27 (4H, s).

EXAMPLE 19

1,4-Bis[4-(1-methyl-1-piperidinio)butyl]benzene dibromide

First, 0.35 g of 1,4-bis(4-bromobutyl)benzene and 0.5 g of N-methylpiperidine were dissolved in 5 ml of absolute ethanol, the solution was refluxed for 9 hours, and evaporated under a reduced pressure. To the residue were added acetone and a small amount of ethanol, and the mixture was stirred at a room temperature for 30 minutes. The resulting crystal was filtered, washed with acetone and dried under a reduced pressure to obtain 0.47 g of the title compound as a colorless crystal.

Melting point: 244° C.

$^1$H—NMR (D 0, δ ppm): 1.53–1.95 (20H, m), 2.09 (4H, t, J=5 Hz), 2.98 (6H, s), 3.14–3.40 (12H, m), 7.26 (4H, s).

REFERENCE EXAMPLE 38

1,4-Bis(5-carboxypentyl)benzene

First, 483 mg of metallic sodium was dissolved in 21 ml of absolute ethanol, and after adding dropwise 6.72 g of diethyl malonate under ice-cooling, the mixture was refluxed for 5 minutes. After cooling, a mixture of 3.48 g of 1,4-bis(4-bromobutyl)benzene and 1.12 g of diethyl malonate was added dropwise at a room temperature, and the mixture was refluxed for 50 minutes. To the resulting white suspension, after cooling, 21 ml of ice water was added. The mixture was adjusted to pH 7.0 with 1N hydrochloric acid, and evaporated under a reduced pressure to remove the ethanol. The aqueous layer was twice extracted with 50 ml of benzene, and the extract was washed with a saturated sodium chloride aqueous solution, dried over magnesium sulfate, and evaporated under a reduced pressure to remove the solvent, and then the remaining diethyl malonate at 140° C. To the colorless oil thus obtained were added 30 ml of acetic acid and 30 ml of concentrated hydrochloric acid, and the mixture was refluxed for 20 hours, and then cooled. The resulting crystal was filtered, washed with water and dried to obtain 2.11 g of the title compound as a colorless crystal.

$^1$H—NMR (DMSO-d6, δ ppm): 1.1–1.4 (4H, m), 1.4–1.6 (8H, m), 2.19 (4H, t, J=7.1 Hz), 2.51 (4H, brt), 7.07 (4H, s), 11.99 (2H, brs).

REFERENCE EXAMPLE 39

1,4-Bis(6-hydroxyhexyl)benzene

To 2.10 g of 1,4-bis(5-carboxypentyl)benzene were added 13 ml of ethanol and 0.69 ml of concentrated sulfuric acid, and the mixture was refluxed for 400 minutes. The reaction mixture was poured into 60 ml of ice water, and adjusted to pH 7.0 with 10% NaOH, evaporated off under a reduced pressure to remove the ethanol, and extracted with total 150 ml of ethyl acetate. The extract was washed with water and a saturated sodium chloride aqueous solution, dried over magnesium sulfate, and evaporated under a reduced pressure to obtain 2.60 g of a colorless oil. A solution of 2.50 g of this oil in 20 ml of absolute tetrahydrofuran was added dropwise with stirring to a suspension of 367 mg lithium aluminium hydride in 21 ml of absolute tetrahydrofuran which had been heated to 60° C., and the mixture was refluxed for an hour. After cooling, to the reaction mixture were successively added 0.37 ml of water, 0.37 ml of 15% sodium hydroxide and 1.1 ml of water with ice-cooling, and the whole was stirred at a room temperature for an hour. The mixture was filtered to remove insoluble materials, and evaporated under a reduced pressure. The residue was applied to a silica gel column and eluted with chloroform/methanol (50:1) to obtain 1.36 g of the title compound as colorless crystal.

$^1$H—NMR (CDCl$_3$, δ ppm): 1.2–1.7 (18H, m), 2.58 (4H, brt), 3.63 (4H, brt), 7.08 (4H, s).

REFERENCE EXAMPLE 40

1,4-Bis(6-dimethylaminohexyl)benzene

To 1.30 g of 1,4-bis(6-hydroxyhexyl)benzene was added 360 μl of phosphorus tribromide with ice-cooling, and the mixture was stirred at a room temperature for 5 minutes and at 80° C. for 70 minutes, and after cooling and adding ice water, extracted twice with 50 ml of ethyl acetate. The extract was washed with water, 5% sodium bicarbonate aqueous solution, water and with a saturated sodium chloride aqueous solution, dried over magnesium sulfate, and evaporated under a reduced pressure. The resulting residue was applied to a silica gel column and eluted with benzene/hexane (3:1) to obtain 1.63 g of 1,4-bis(6-bromohexyl)benzene as a colorless liquid.

$^1$H—NMR (CDCl$_3$, δ ppm): 1.22–1.95 (16H, m), 2.59 (4H, t, J=7.0 Hz), 3.40 (4H, t, J=7.0 Hz), 7.10 (4H, s).

Next, 0.40 g of the colorless liquid thus obtained and 0.9 ml of 50% aqueous dimethylamine solution were added to a mixture of 2 ml of ethanol and 0.5 ml of chloroform. The mixture was stirred at a room temperature for 2 hours, and evaporated under a reduced pressure to remove the solvent. To the residue was added chloroform, which was then evaporated off under a reduced pressure, and after adding ethyl acetate the mixture was extracted with 15 ml of 1N hydrochloric acid. The aqueous extract was alkalized with 10% sodium hydroxide and extracted with total 80 ml of chloroform. The extract was washed with water and sodium chloride aqueous solution, dried over magnesium sulfate, and evaporated under a reduced pressure to obtain 0.33 g of the title compound as a pale yellow liquid.

$^1$H—NMR (CDCl$_3$, δ ppm): 1.24–1.69 (16H, m), 2.11–2.30 (12H+4H, m), 2.58 (4H, t, J=7.0 Hz), 7.1 (4H, s).

EXAMPLE 20

1,4-Bis(6-trimethylammoniohexyl)benzene diiodide

First, 0.35 g of 1,4-bis(6-dimethylaminohexyl)benzene and 1.42 g of methyl iodide were dissolved in 5 ml of absolute methanol, and the mixture was refluxed for 2 hours, cooled to a room temperature, and further cooled with ice/sodium chloride. The resulting crystal was filtered, washed with methanol and dried under a reduced pressure to obtain 0.353 g of the title compound as a pale yellow crystal.

Melting point: 223° C.;

$^1$H—NMR (D$_2$O, δ ppm): 1.20–1.82 (16H, m), 2.59 (4H, t, J=7.0 Hz), 3.08 (18H, s), 3.16–3.36 (4H, m), 7.20 (4H, s).

REFERENCE EXAMPLE 41

1,4-Bis(6-diethylaminohexyl)benzene

First, 0.42 g of 1,4-bis(6-bromohexyl)benzene and 0.44 g of diethylamine were dissolved in 5 ml of absolute ethanol, and the mixture was refluxed for 2 hours. After removing the solvent under a reduced pressure and adding chloroform, the mixture was evaporated under a reduced pressure. The residue was acidified with 1N hydrochloric acid, washed with chloroform, alkalized with 10% sodium hydroxide, subjected to salting out, and extracted with total 80 ml of chloroform. The extract was washed with water and a saturated sodium chloride aqueous solution, dried over magnesium sulfate, and evaporated under a reduced pressure to obtain 0.37 g of the title compound as a pale yellow liquid.

$^1$H—NMR (CDCl$_3$, δ ppm): 1.05 (12H, t, J=7.0 Hz), 1.15–1.71 (16H, m), 2.31–2.63 (16H, m), 7.08 (4H, s).

EXAMPLE 21

1,4-Bis(6-triethylammoniohexyl)benzene diiodide

First, 300 mg of 1,4-bis(6-diethylaminohexyl)benzene were dissolved in 3 ml of absolute ethanol, and after adding 616 μl of ethyl iodide, the mixture was stirred at a room temperature for 30 minutes, refluxed for 1.5 hours, and then cooled. The mixture was evaporated under a reduced pressure, and after adding 3 ml of acetone, evaporated under a reduced pressure. The residue was dissolved in 1.5 ml of acetone, and the solution was allowed to stand in a freezer for 2 days. The resulting crystal was collected by filtration, washed with ethyl acetate and dried under a reduced pressure to obtain 490 mg of the title compound as a colorless crystal.

Melting point: 153°–155° C.;

$^1$H—NMR (D$_2$O, δ ppm): 1.23 (18H, brt), 1.35 (8H, brs), 1.58 (8H, brs), 2.58 (4H, brt), 3.0–3.2 (4H, m), 3.23 (12H, brq), 7.18 (4H, s).

EXAMPLE 22

1,4-Bis[6-(1-methyl-1-piperidinio)hexyl]benzene dibromide

First, 0.28 g of 1,4-bis(6-bromohexyl)benzene and 0.5 g of N-methylpiperidine were dissolved in 4 ml of absolute ethanol, and the mixture was refluxed for 2 hours and evaporated under a reduced pressure to remove the solvent. After adding acetone and then ethanol, the whole was allowed to stand in a freezer for 3 days. The resulting crystal was collected by filtration, washed with acetone and dried under a reduced pressure to obtain 0.125 g of the title compound as a colorless crystal.

Melting point: 205° C.;

$^1$H—NMR (D$_2$O, δ ppm): 1.27–1.95 (28H, m), 2.61 (4H, t, J=7.0 Hz), 2.99 (6H, s), 3.17–3.36 (12H, m), 7.25 (4H, s).

REFERENCE EXAMPLE 42

1,4-Bis(4-bromobutyl)-2-nitrobenzene

To 1 ml of 60% nitric acid was added 1 ml of 97% sulfuric acid under ice-cooling, and the mixture was stirred for 10 minutes. After adding 0.42 g of 1,4-bis(4-bromobutyl)benzene, the whole was stirred at a room temperature for an hour. The reaction mixture was poured onto ice, and extracted with total 60 ml of chloroform. The extract was washed with a saturated sodium chloride aqueous solution, dried over magnesium sulfate and evaporated under a reduced pressure to remove the solvent. The residue was applied to a silica gel column and eluted with chloroform/hexane (1:1). From the first fraction, 0.43 g of the title compound was obtained as a pale yellow liquid.

$^1$H—NMR (CDCl$_3$, δ ppm): 1.60–2.02 (8H, m), 2.70 (2H, t, J Hz), 2.88 (2H, t, J=7.0 Hz), 3.34–3.50 (4H, m), 7.28 ($^1$H, d, J=7.0 Hz), 7.37 ($^1$H, dd, J=7.0, 2.0 Hz), 7.73 ($^1$H, d, J=2.0 Hz).

REFERENCE EXAMPLE 43

1,4-Bis(4-dimethylaminobutyl)-2-nitrobenzene

To 2 ml of ethanol were added 0.42 g of 1,4-bis(4-bromobutyl)-2-nitrobenzene and 0.9 ml of 50% aqueous dimethylamine solution, and the mixture was stirred at a room temperature for 4 hours and evaporated under a reduced pressure. After adding chloroform, the mixture was evaporated under a reduced pressure, to which was then added ethyl acetate, and the whole was extracted with 15 ml of 1N hydrochloric acid. The aqueous extract was alkalized with 10% sodium hydroxide and extracted with total 60 ml of chloroform. The organic extract was washed with water and a saturated sodium chloride aqueous solution and dried over magnesium sulfate, and evaporated under a reduced pressure to obtain 0.28 g of the title compound as a pale yellow liquid.

$^1$H—NMR (CDCl$_3$, δ ppm): 1.42-1.76 (8H, m), 2.13-2.36 (12H+4H, m), 2.69 (2H, t, J=7.0 Hz), 2.88 (2H, t, J=7.0 Hz), 7.25 ($^1$H, d, J=8.0 Hz), 7.33 ($^1$H, dd, J=8.0, 1.0 Hz), 7.72 ($^1$H, d, J=1.0 Hz).

EXAMPLE 23

1,4-Bis(4-trimethylammoniobutyl)-2-nitrobenzene diiodide

First, 0.5 g of 1,4-bis(4-dimethylaminobutyl)-2-nitrobenzene and 2.0 g of methyl iodide were dissolved in 10 ml of absolute methanol, and the solution was refluxed for 2 hours. After cooling, the resulting crystal was recovered by filtration, washed with ethanol, dried under a reduced pressure, and then dissolved in 1 ml of water. The aqueous solution was lyophilized to obtain 0.164 g of the title compound as a hygroscopic pale yellow amorphous.

$^1$H—NMR (D$_2$O, δ ppm): 1.58-1.98 (8H, m), 2.63-2.99 (4H, m), 3.10 (9H, s), 3,12 (9H, s), 3.25-3.43 (4H, m), 7.44 ($^1$H, d, J=8.0 Hz), 7.53 ($^1$H, dd, J=8.0, 1.0 Hz), 7.88 ($^1$H, d, J=1.0 Hz).

REFERENCE EXAMPLE 44

2-Amino-1,4-bis(4-dimethylaminobutyl)benzene

To a solution of 3.5 g of 1,4-bis(4-dimethylaminobutyl)-2-nitrobenzene in 120 ml of methanol, 9 ml of 6N hydrochloric acid and 1.5 g of 5% palladium/carbon were added. The catalytic reduction was carried out under an atmospheric pressure and at a room temperature. When about 710 ml of hydrogen was absorbed after one hour, the reaction was terminated, and the reaction mixture was filtered to remove the catalyst and evaporated under a reduced pressure. After adding chloroform, the mixture was again evaporated under a reduced pressure. The residue was alkalized with 10% sodium hydroxide, subjected to salting out and extracted twice with 50 ml of chloroform. The extract was washed with water and a saturated sodium chloride aqueous solution and dried over magnesium sulfate. The solvent was removed under a reduced pressure to obtain 2.7 g of the title compound as a pale brown liquid.

$^1$H—NMR (CDCl$_3$, δ ppm): 1.40-1.71 (8H, m), 2.18-2.60 (12H+8H, m), 3.60 (2H, brs), 6.47-6.58 (2H, m), 6.93 ($^1$H, d, J=7.0 Hz).

REFERENCE EXAMPLE 45

2-Acetylamino-1,4-bis(4-dimethylaminobutyl)benzene

To 1 ml of acetic anhydride was added 0.58 g of 2-amino-1,4-bis(4-dimethylaminobutyl)benzene, and the solution was stirred at 50° C. for 2.5 hours. After adding 8 ml of 5% sodium carbonate, the mixture was stirred at a room temperature for 5 hours, alkalized with 10% sodium hydroxide, subjected to salting out and extracted with total 70 ml of chloroform. The extract was washed with a saturated sodium chloride aqueous solution, dried over potassium carbonate, and evaporated under a reduced pressure to obtain 0.56 g of the title compound as a pale brown crystal.

$^1$H—NMR (CDCl$_3$, δ ppm): 1.38-1.75 (8H, m), 2.10-2.39 (19H, m), 2.42-2.68 (4H, m), 6.81-7.12 (2H, m), 7.65 (1H, s).

EXAMPLE 24

2-Acetylamino-1,4-bis(4-trimethylammoniobutyl)benzene diiodide

First, 0.55 g of 2-acetylamino-1,4-bis(4-dimethylaminobutyl)benzene and 2.0 g of methyl iodide were dissolved in 5 ml of absolute methanol, and the solution was refluxed for 2.5 hours and evaporated under a reduced pressure. After adding methanol and then acetone, the mixture was kept in a freezer for 2 weeks, The resulting crystal was collected by filtration, washed with acetone and dried under a reduced pressure to obtain 0.13 g of the title compound as a pale yellow crystal.

Melting point: 223° C.;

$^1$H—NMR (D$_2$O, δ ppm): 1.42-1.96 (8H, m), 2.24 (3H, s), 2.48-2.84 (4H, m), 3.10 (18H, s), 3.22-3.48 (4H, m), 7.19 ($^1$H, s), 7.28 ($^1$H, d, J=7.0 Hz), 7.38 ($^1$H, d, J=7.0 Hz).

REFERENCE EXAMPLE 46

1,4-Bis[4-(p-toluenesulfonyloxy)-1-butynyl]benzene

To a solution of, 1.71 g of 1,4-bis(4-hydroxy-1-butynyl)benzene in 10 ml of pyridine, 3.05 g of p-toluenesulfonyl chloride was added, and the mixture was stirred at a room temperature for an hour. After adding 10 ml of tetrahydrofuran, the mixture was stirred at a room temperature for an hour and filtered. The filtrate was evaporated under a reduced pressure, and after adding water, extracted twice with 50 ml of chloroform. The extract was washed with a saturated sodium chloride aqueous solution, dried over magnesium sulfate and evaporated under a reduced pressure. The residue was applied to a silica gel column and eluted with chloroform/hexane (1:1) to obtain 1.80 g of the title compound as a pale yellow crystal.

$^1$H—NMR (CDCl$_3$, δ ppm): 2.44 (6H, s), 2.80 (4H, t, J=7.0 Hz), 4.19 (4H, t, J=7.0 Hz), 7.17-7.45 (8H, m), 7.82 (4H, d, J=8.0 Hz).

REFERENCE EXAMPLE 47

1,4-Bis(4-dimethylamino-1-butynyl)benzene

To a mixture of 20 ml ethanol and 30 ml chloroform were added 1.8 g of 1,4-bis[4-(p-toluenesulfonyloxy)-1-butynyl]benzene and 9 ml of 50% dimethylamine, the mixture was stirred at a room temperature for 20 hours, and evaporated under a reduced pressure. After adding chloroform, the mixture was evaporated under a reduced pressure. To the residue was added water, and the mixture was acidified with 1N hydrochloric acid, washed with chloroform, alkalized with 10% sodium hydroxide to salting out, and extracted with total 70 ml of chloroform. The extract was washed with a saturated sodium chloride aqueous solution and dried over magnesium sulfate, and was evaporated under a reduced pressure to obtain 0.43 g of the title compound as a pale yellow liquid.

$^1$H—NMR (CDCl$_3$, δ ppm): 2.32 (12H, s), 2.51-2.55 (8H, m), 7.31 (4H, s).

EXAMPLE 25

1,4-Bis(4-trimethylammonio-1-butynyl)benzene diiodide

First, 0.4 g of 1,4-bis(dimethylamino-1-butynyl)benzene and 2.13 g of methyl iodide were dissolved in 7 ml of absolute methanol, and the solution was refluxed for 2 hours. The mixture was cooled to a room temperature and kept in a freezer for a month. The resulting crystal was collected by filtration, washed with acetone and dried under a reduced pressure to obtain 0.38 g of the title compound as a pale yellow crystal.

Melting point: 240° C.;

$^1$H—NMR (D$_2$O, δ ppm): 3.08 (4H, t, J=7.0 Hz), 3.23 (18H, s), 3.66 (4H, t, J=7.0 Hz), 7.47 (4H, s).

REFERENCE EXAMPLE 48

1,4-Bis(4-dimethylaminobutyl)benzene

To a solution of 2.01 g lithium aluminium hydride in 24 ml of tetrahydrofuran was added dropwise a solution of 7.04 g aluminium chloride in 36 ml of ethyl ether at a room temperature for 10 minutes, and after stirring for 10 minutes, a solution of 5.09 g 1,4-bis(3-cyanopropyl)benzene in 48 ml of tetrahydrofuran was added dropwise over 30 minutes, and the mixture was stirred for 5 hours. To the reaction mixture were successively added 2.0 ml of water, 15% sodium hydroxide aqueous solution and a solution of 6.34 g of sodium hydroxide in 6 ml of water. The mixture was stirred for 30 minutes, filtered to remove impurity and washed with tetrahydrofuran. The washed filtrate was concentrated under a reduced pressure, codistilled twice with tetrahydrofuran and twice with chloroform, and dried under a reduced pressure to obtain 5.36 g of 1,4-bis(4-aminobutyl)benzene as yellow liquid.

This product conforms to a compound described in J. Chem. Soc. Perkin Trans. 1,3125 ('81) on NMR data.

To 4.84 g of 1,4-bis(4-aminobutyl)benzene obtained above were added 8.4 ml of formic acid and 7.9 ml of 37% formaldehyde aqueous solution, and the mixture was refluxed for 8 hours and then cooled. After adding 5.0 ml of concentrated hydrochloric acid, the mixture was evaporated at 100° C. under a reduced pressure to remove extra formic acid and water. The residue was alkalized to pH 12 with 10% sodium hydroxide aqueous solution, salted out with sodium chloride, and extracted three times with 100 ml of chloroform. The combined extract was washed with a saturated sodium chloride aqueous solution and dried over magnesium sulfate, evaporated under a reduced pressure, and dried under a reduced pressure to obtain 6.34 g of the title compound as an orange-colored liquid.

$^1$H—NMR (CDCl$_3$, δ ppm): 1.55 (8H, m), 2.22 (12H, s), 2.29 (4H, brt), 2.59 (4H, t, J=7.5 Hz), 7.09 (4H, s).

REFERENCE EXAMPLE 49

1,4-Bis(6-diethylaminohexyl)-2-nitrobenzene

With ice-cooling, to 2 ml of 60% nitric acid was added 2 ml of 97% sulfuric acid, and after stirring for 10 minutes, 2.3 g of 1,4-bis(6-bromohexyl)benzene was added. After stirring with ice-cooling for 5 hours, 20 g of ice and then water were added, and the mixture was extracted with 100 ml and 50 ml of chloroform. The extracts were combined, washed with a saturated sodium chloride aqueous solution, dried over magnesium sulfate and evaporated under a reduced pressure to obtain 2.0 g of a residue. The residue was applied to a silica gel column and eluted with chloroform/hexane (3:7). From the first fraction, 1.80 g of 1,4-bis(6-bromohexyl)-2-nitrobenzene was obtained as a pale yellow liquid.

$^1$H—NMR (CDCl$_3$, δ ppm): 1.20-1.97 (16H, m), 2.68 (2H, t, J=7 Hz), 2.86 (2H, t, J=7 Hz), 3.42 (4H, t, J=7 Hz), 7.25 (1H, d, J=8 Hz), 7.33 (1H, dd, J=8, 2 Hz), 7.70 (1H, d, J=2 Hz).

To a solution of 0.9 g of the pale yellow liquid thus obtained in a mixture of 10 ml ethanol and 3 ml chloroform, 0.73 g of diethyl amine was added, and the mixture was refluxed for 2 hours. The reaction mixture was evaporated under a reduced pressure, and after adding ethyl acetate, extracted with 20 ml and 10 ml of 1N hydrochloric acid. The combined extract was alkalized with 10% sodium hydroxide, and extracted twice with 50 ml of ethyl acetate. The extract was washed with water and a saturated sodium chloride aqueous solution, dried over magnesium sulfate, and evaporated under a reduced pressure to obtain 0.60 g of the title compound as a pale yellow liquid.

$^1$H—NMR (CDCl$_3$, δ ppm): 1.03 (12H, t, J=7 Hz), 1.15-1.72 (16H, m), 2.25-2.71 (14H, m), 2.84 (2H, t, J=7 Hz), 7.23 (1H, d, J=8 Hz), 7.32 (1H, dd, J=8,2 Hz), 7.68 (1H, d, J=2Hz).

EXAMPLE 26

1,4-Bis(6-triethylammoniohexyl)-2-nitrobenzene diiodide

First, 600 mg of 1,4-bis(6-diethylaminohexyl)-2-nitrobenzene was dissolved in 7 ml of absolute ethanol, and after adding 2.18 g of ethyl iodide at a room temperature with stirring, the mixture was refluxed for 3 hours and then cooled. The reaction mixture was evaporated under a reduced pressure, diluted with 3 ml of acetone, and after adding 1 ml of ethyl acetate allowed to stand in a freezer overnight. Resulting crystal was collected by filtration, washed with acetone/ethyl acetate (1:1), and dried under a reduced pressure to obtain 555 mg of the title compound as a pale yellow crystal.

Melting point: 115° C.-117° C. (decomposed);

$^1$H-NMR (D 0, δ ppm): 1.27 (18H, brt), 1.39 (8H, brs), 1.64 (8H, brs), 2.68 (2H, brt), 2.82 (2H, brt), 3.15 (4H, brt), 3.28 (12H, brq), 7.40 (1H, d, J=7.6 Hz), 7.50 (1H, brd), 7.75 (1H, brs).

REFERENCE EXAMPLE 50

1,4-Bis(6-ethoxycarbonyl)-3-hexenyl)benzene

First, 2.78 g of 1,4-bis(2-ethoxycarbonylethyl)benzene was dissolved in 40 ml of absolute toluene, the solution was cooled to −65° C. with dry ice/acetone, and a solution of 1M diisobutylammonium hydride in 24 ml of toluene was added dropwise with stirring over 25 minutes, and the mixture was further stirred at −70° C. for 2 hours. Next, 2.5 ml of ethanol/2.5 ml of toluene, 3 ml of ethanol, and 2.75 ml of water/5.5 ml of ethanol were added dropwise in this order, and after removing cooling bath, the mixture was allowed to warm to a room temperature with stirring. After adding 10 ml of water, the mixture was adjusted to a pH value of not more than 3 with 6N hydrochloric acid. The organic layer was separated, washed with water and a saturated sodium chloride aqueous solution, dried over magnesium sulfate, and evaporated under a reduced pressure. The residue was applied to a silica gel column and eluted with hexane/ethyl acetate (6:1) to obtain 988 mg of 1,4-bis(2-formylethyl)benzene as a colorless crystal.

¹H—NMR (CDCl₃, & ppm): 2.7-2.8 (4H, m), 2.8-3.0 (4H, m), 7.12 (4H, s), 9.82 (2H, t, J=1.4 Hz).

Sodium ethoxide prepared from 292 mg of sodium was dissolved in 22 ml of absolute dimethylformamide, to the solution was added at once 6.76 g of ethoxycarbonylpropyl triphenylphosphonium bromide under nitrogen flow at a room temperature, and the mixture was stirred for 2 hours. To this mixture was added dropwise a solution of 966 mg of the colorless crystal obtained above in 7.3 ml of absolute dimethylformamide at 5° C. over 5 minutes. Next, the mixture was stirred for 30 minutes with ice-cooling and then at a room temperature overnight, poured on water 100 ml/ethyl acetate 50 ml, and filtered to remove the insoluble matter. The aqueous layer was separated, and extracted with 50 ml of ethyl acetate. The combined extract was washed twice with water and a saturated sodium chloride aqueous solution, dried over magnesium sulfate, filtered, and evaporated under a reduced pressure. The residue was applied to a silica gel column and eluted with chloroform to obtain 707 mg of the title compound as a colorless liquid.

¹H—NMR (CDCl₃, δ ppm): 1.25 (6H, t, J=7.1 Hz), 2.2-2.4 (12H, m), 2.63 (4H, brt), 4.12 (4H, q, J=7.1 Hz), 5.3-5.5 (4H, m), 7.10 (4H, s).

REFERENCE EXAMPLE 51

1.4-Bis(7-bromoheptyl)benzene

First, 707 mg of 1,4-bis(6-ethoxycarbonyl-3-hexenyl)benzene was dissolved in 14 ml of ethanol, and after adding 70 mg of 5% palladium/carbon, the mixture was stirred under hydrogen flow at a room temperature for 2 hours, filtered to remove the catalyst, and concentrated under a reduced pressure to obtain 601 mg of 1,4-bis(6-ethoxycarbonylhexyl)benzene as a colorless liquid.

¹H—NMR (CDCl₃, δ ppm): 1.25 (6H, t, J=7.1 Hz), 1.34 (8H, brs), 1.61 (8H, brs), 2.28 (4H, t, J=7.5 Hz), 2.56 (4H, t, J=7.6 Hz), 4.12 (4H, q, J=7.1 Hz), 7.07 (4H, s).

A solution of 601 mg of the colorless liquid thus obtained in absolute tetrahydrofuran was added dropwise to a suspension of 82 mg lithium aluminium hydride in 4.5 ml of absolute tetrahydrofuran with stirring at 50° C.-60° C. over 25 minutes, and the mixture was refluxed for 3 hours.

During the reaction, 82 mg of lithium aluminium hydride was added in two portions to complete the reaction. After adding 250 μl of water, 250 μl of 15% sodium hydroxide and 750 μl of water under ice-cooling, the mixture was stirred at a room temperature for 2 hours and filtered to remove insoluble matter. The filtrate was evaporated under a reduced pressure, and after adding 119 μl of phosphorus tribromide at a room temperature, the mixture was stirred for an hour at 80° C. After cooling and adding ice water, the mixture was extracted with 50 ml of ethyl acetate. The extract was successively washed with water, 5% sodium bicarbonate aqueous solution, water and a saturated sodium chloride aqueous solution, dried over magnesium sulfate, filtered, and evaporated under a reduced pressure. The residue was applied to silica gel column and eluted with hexane/benzene (10:1) to obtain 332 mg of the title compound as a colorless crystal.

¹H—NMR (CDCl₃, δ ppm): 1.35 (12H, brs), 1.60 (4H, brs), 1.7-1.9 (4H, m), 2.57 (4H, brt), 3.39 (4H, t, J=6.8 Hz), 7.08 (4H, s).

REFERENCE EXAMPLE 52

1,4-Bis(7-diethylaminoheptyl)benzene

To a solution of 150 mg of 1,4-bis(7-bromoheptyl)benzene in 0.35 ml of ethanol and 0.18 ml of water was added 181 μl of diethylamine, and the mixture was refluxed for 2 hours. After adding 50 ml of ethyl acetate, the mixture was washed with 5% sodium bicarbonate aqueous solution, water and a saturated sodium chloride aqueous solution, dried over magnesium sulfate, filtered, and evaporated under a reduced pressure to obtain 97 mg of the title compound as a pale brown liquid.

¹H—NMR (CDCl₃, δ ppm): 1.01 (12H, t, J=7.1 Hz), 1.32 (12H, brs), 1.41 (4H, brs), 1.59 (4H, brs), 2.39 (4H, brt), 2.51 (8H, q, J=7.1 Hz), 2.57 (4H, brt), 7.07 (4H, s).

EXAMPLE 27

1,4-Bis(7-triethylammonioheptyl)benzene diiodide

To solution of 97 mg of 1,4-bis(7-diethylaminoheptyl)benzene in 1 ml of absolute ethanol, was added 187 μl of ethyl iodide, and the mixture was refluxed for 3 hours and evaporated under a reduced pressure. After adding acetone, the mixture was concentrated and allowed to stand in a freezer for a week to obtain 152 mg of the title compound as a pale brown crystal.

¹H—NMR (D₂O, δ ppm): 1.29 (18H, brt), 1.30 (12H, brs), 1.55 (8H, brs), 2.53 (4H, brt), 3.07 (4H, brs), 3.25 (12H, brq), 7.13 (4H, brs).

REFERENCE EXAMPLE 53

1,4-Bis(3-hydroxypropylthio)benzene

First, 1.03 g of p-dichlorobenzene was dissolved in 35 ml of absolute hexamethylphosphoric amide, and after adding 2.06 g of sodium isopropylmercaptan, the mixture was stirred at 80° C. for 4 hours. Next, the reaction mixture was heated to 100° C., and after adding 419 mg of metallic sodium in ten portions over 15 minutes, stirred for 3 hours to obtain a dark red suspension. After ice-cooling and adding dropwise 3.06 g of 3-bromopropanol in 2 ml of absolute hexamethylphosphoric amide over 3 minutes, the mixture was stirred at a room temperature overnight. The resulting yellow suspension was poured into 300 ml of ice water, and successively extracted with 100 ml, 50 ml and 50 ml of ethyl ether. The extracts were combined, washed with water, a saturated sodium chloride aqueous solution and water, dried over anhydrous magnesium sulfate, filtered, and evaporated under a reduced pressure. The obtained ograngeoil was applied to a silica gel column and eluted with hexane/ethyl acetate (2:1) to obtain 1.04 g of the title compound as a colorless crystal.

EI Mass m/z: 258 (M+);

¹H—NMR (CDCl₃, δ ppm): 1.60 (2H, brs), 1.8-2.0 (4H, m), 3.02 (4H, t, J=7.1 Hz), 3.75 (4H, t, J=6.1 Hz), 7.27 (4H, s).

REFERENCE EXAMPLE 54

1,4-Bis(3-dimethylaminopropylthio)benzene

To 640 mg of 1,4-bis(3-hydroxypropylthio)benzene was added 191 μl of phosphorus tribromide with ice-cooling, and the mixture was stirred at 80° C. for 2 hours, and after adding ice-water extracted with 50 ml of ethyl acetate. The extract was washed twice with water, 3% sodium bicarbonate aqueous solution, water and with a saturated sodium chloride aqueous solution, dried over magnesium sulfate, filtered, and evaporated under a reduced pressure to remove the solvent. The residue was applied to a silica gel column and eluted with hexane/ethyl acetate (50:1) to obtain 719 mg of 1,4-bis(3-bromopropylthio)benzene as a colorless liquid.

EI Mass m/z: 382 (M+);

$^1$H—NMR (CDCl$_3$, δ ppm): 2.0–2.2 (4H, m), 3.05 (4H, t, J=7.0 Hz), 3.52 (4H, t, J=6.3 Hz), 7.28 (4H, s).

To a solution of 191 mg of the liquid obtained in 260 μl of ethanol, 260 μl of 50% aqueous dimethylamine solution was added dropwise at a room temperature with stirring, and the mixture was stirred for 7 hours. After adding 10 ml of 5% sodium bicarbonate aqueous solution, the reaction mixture was extracted with 50 ml of benzene. The extract was washed with water and a saturated sodium chloride aqueous solution, dried over magnesium sulfate, filtered, and then evaporated under a reduced pressure to obtain 125 mg of the title compound as a colorless liquid.

$^1$H—NMR (CDCl$_3$, δ ppm): 1.7–1.9 (4H, m), 2.20 (12H, s), 2.37 (4H, t, J=7.2 Hz), 2.92 (4H, t, J=7.2 Hz), 7.25 (4H, s).

EXAMPLE 28

1,4-Bis(3-trimethylammoniopropylthio)benzene diiodide

To a solution of 124 mg of 1,4-bis(dimethylaminopropylthio)benzene dissolved in 1 ml of absolute methanol, was added dropwise 248 μl of methyl iodide at a room temperature with stirring and stirred for 2 hours, and the mixture was refluxed for 30 minutes and then cooled. The resulting crystal was collected by filtration, washed with methanol and acetone, and dried under a reduced pressure to obtain 190 mg of the title compound as colorless crystal.

Melting point: 247° C.–248° C. (decomposed);

$^1$H—NMR (D$_2$O, δ ppm): 2.0–2.2 (4H, brm), 3.0–3.1 (4H, m), 3.08 (18H, s), 3.4–3.5 (4H, m), 7.45 (4H, s).

REFERENCE EXAMPLE 55

1,4-Bis(3-dimethylaminopropylsulfinyl)benzene

First, 191 mg of 1,4-bis(3-bromopropylthio)benzene was dissolved in 2.5 ml of absolute methylene chloride, and after adding 190 mg of m-chloroperbenzoic acid with stirring and ice-cooling, the mixture was stirred for 2 hours with ice-cooling. After adding 10 ml of 5% sodium bicarbonate, the reaction mixture was extracted with 50 ml of chloroform. The extract was washed with water and a saturated sodium chloride aqueous solution, dried over magnesium sulfate, filtered and evaporated under a reduced pressure. The residue was applied to a silica gel column and eluted with ethyl acetate to obtain 207 mg of 1,4-bis(3-bromopropylsulfinyl)benzene as a colorless crystal.

EI Mass m/z: 414 (M+);

$^1$H—NMR (CDCl$_3$, δ ppm): 2.1–2.3 (2H, m), 2.3–2.5 (2H, m), 2.8–3.0 (2H, m), 3.0–3.2 (2H, m), 3.4–3.6 (4H, m), 7.81 (4H, s).

To a suspension of 207 mg of the colorless crystal thus obtained in 0.5 ml of ethanol, was added 0.5 ml of 50% dimethylamine aqueous solution at a room temperature with stirring, and the mixture was stirred for 3 hours to obtain a colorless solution. After adding 10 ml of 5% sodium bicarbonate aqueous solution the reaction mixture was extracted with 30 ml, 20 ml and 20 ml of chloroform. The combined extracts were washed with a saturated sodium chloride aqueous solution, dried over magnesium sulfate, filtered, and evaporated under a reduced pressure to obtain 88 mg of the title compound as a colorless crystal.

$^1$H—NMR (CDCl$_3$, δ ppm): 1.7–2.1 (4H, m), 2.18 (12H, s), 2.3–2.5 (4H, m), 2.7–3.1 (4H, m), 7.78 (4H, s).

EXAMPLE 29

1,4-Bis(3-trimethylammoniopropylsulfinyl)benzene diiodide

To a solution of 88 mg of 1,4-bis(3-dimethylaminopropylsulfinyl)benzene in 1 ml of absolute methanol, was added dropwise 159 μl of methyl iodide at a room temperature with stirring. The mixture was stirred for 3 hours, refluxed for 30 minutes, then cooled, and concentrated under a reduced pressure. After adding 0.5 ml of acetone, the mixture was allowed to stand for an hour. The resulting crystal was collected by filtration, washed with acetone and hexane, and dried under a reduced pressure to obtain 120 mg of the title compound as a colorless crystal.

Melting point: 172° C.–174° C. (decomposed);

$^1$H—NMR (D$_2$O, δ ppm): 2.0–2.5 (4H, m), 3.1–3.3 (4H, m), 3.14 (18H, s), 3.4–3.6 (4H, m), 7.96 (4H, s).

REFERENCE EXAMPLE 56

1,4-Bis(3-dimethylaminopropylsulfonyl)benzene

First, 150 mg of 1,4-bis(3-bromopropylthio)benzene was dissolved in 5 ml of drymethylene chloride, and after adding 339 mg of m-chloroperbenzoic acid with stirring and ice-cooling, the mixture was stirred with ice-cooling for 30 minutes and then at a room temperature for 40 minutes. After adding 50 ml of chloroform, the reaction mixture was washed with 5% sodium bicarbonate aqueous solution, water and a saturated sodium chloride aqueous solution, dried over a magnesium sulfate, filtered and evaporated under a reduced pressure to obtain 174 mg of 1,4-bis(3-bromopropylsulfonyl)benzene as a colorless crystal.

$^1$H—NMR (CDCl$_3$, δ ppm): 2.2–2.4 (4H, m), 3.34 (4H, brt), 3.50 (4H, t, J=6.2 Hz), 8.16 (4H, s).

Next, 174 mg of the crystal thus obtained was suspended in 0.5 ml of ethanol, and after adding 0.5 ml of 50% dimethylamine aqueous solution the mixture was stirred overnight. After adding 1 ml of tetrahydrofuran, the clear solution was further stirred for 7 hours. After adding water, the reaction mixture was extracted twice with 20 ml and 10 ml of benzene. The extract was washed with a saturated sodium chloride aqueous solution, dried over magnesium sulfate, filtered and evaporated under a reduced pressure to obtain 119 mg of the title compound as a colorless crystal.

$^1$H—NMR (CDCl$_3$, δ ppm): 1.8–2.0 (4H, m), 2.15 (12H, s), 2.33 (4H, t, J=6.6 Hz), 3.22 (4H, brt), 8.13 (4H, s).

EXAMPLE 30

1,4-Bis(3-trimethylammoniopropylsulfonyl)benzene diiodide

To a solution of 119 mg of 1,4-bis(3-dimethylaminopropylsulfonyl)benzene in 1 ml of absolute methanol, was added dropwise 197 μl of methyl iodide at a room temperature with stirring, and the mixture was stirred for 1.5 hours, refluxed for 30 minutes and cooled. After adding 1 ml of acetone the reaction mixture was stirred for 30 minutes. The resulting crystal was collected by filtration, washed with acetone, and evaporated under a reduced pressure to obtain 193 mg of the title compound as a pale yellow crystal.

Melting points: 102° C.-105° C. (decomposed);

$^1$H—NMR (D$_2$O, δ ppm): 2.2-2.4 (4H, m), 3.15 (18H, s), 3,4-3.7 (8H, m), 8.29 (4H, s).

REFERENCE EXAMPLE 57

2.6-Bis(bromomethyl)naphthalene

To 5.84 g of dipotassium 2,6-naphthalenedicarbonate was added 14.6 ml of thionyl chloride, and the mixture was refluxed for 5 hours and cooled. The mixture was evaporated under a reduced pressure to remove the thionyl chloride, and after adding 45 ml of ethanol, the mixture was refluxed for 90 minutes. After cooling, the resulting crystal was collected by filtration and dried under a reduced pressure to obtain 4.91 g of diethyl 2,6-naphthalenedicarboxylate as a colorless crystal.

$^1$H-NMR (CDCl$_3$, δ ppm): 1.46 (6H, t, J=7.1 Hz), 4.46 (4H, q, J=7.1 Hz), 7.99 (2H, d, J=8.6 Hz), 8.13 (2H, dd, J=1.7, 8.6 Hz), 8.63 (2H, d, J=1.7 Hz).

To a solution of 1.67 g of the crystal described above in 25 ml of absolute tetrahydrofuran was added in small portions 327 mg of lithium aluminium hydride over 10 minutes at a room temperature with stirring, and the mixture was stirred at a room temperature for 40 minutes. To the reaction mixture were successively added 0.33 ml of water, 0.33 ml of 15% sodium hydroxide and 1 ml of water with ice-cooling, and the mixture was stirred at a room temperature for 50 minutes, filtered to remove insoluble matter and concentrated under a reduced pressure. Resulting crude crystal was dissolved in 8 ml of hot tetrahydrofuran, and after adding 16 ml of ethyl acetate the mixture was allowed to stand overnight. The resulting crystal was collected by filtration, washed with ethyl acetate and dried under a reduced pressure. The obtained crystal was suspended in 20 ml of absolute tetrahydrofuran, and after adding dropwise 498 μl of phosphorus tribromide at a room temperature with stirring, the mixture was refluxed for 9 hours, filtered under heating to remove insoluble matter, and concentrated under a reduced pressure. After adding 5 ml of ethyl acetate, the mixture was allowed to stand for 30 minutes. The resulting crystal was collected by filtration, washed with ethyl acetate and dried under a reduced pressure to obtain 1.21 g of the title compound as a colorless crystal.

$^1$H—NMR (CDCl$_3$, δ ppm): 4.66 (4H, s), 7.52 (2H, dd, J=1.5, 8.6 Hz), 7.81 (2H, d, J=8.6 Hz), 7.82 (2H, d, J=1.5 Hz).

REFERENCE EXAMPLE 58

2,6-Bis(2-carboxyethyl)naphthalene

First, 228 mg of metallic sodium was dissolved in 10 ml of absolute ethanol, and after adding 3.02 g of diethyl malenate, the mixture was refluxed for 5 minutes and cooled. After adding 504 mg of diethyl malonate and then 1.41 g of 2,6-bis(bromomethyl)naphthalene at once, the mixture was refluxed 2 hours. After cooling and adding 20 ml of ice water, the reaction mixture was adjusted to pH 6.0 with 1N hydrochloric acid and extracted twice with 100 ml of benzene. The extracts were combined, washed with water and a saturated sodium chloride aqueous solution, dried over magnesium sulfate, filtered, and evaporated under a reduced pressure. To the resulting pale yellow oil were added 15 ml of acetic acid and 15 ml of concentrated hydrochloric acid, and the mixture was refluxed for 23 hours, cooled and concentrated. After adding 5 ml of water, the resulting crystal was collected by filtration, washed with water and dried in air and then under a reduced pressure to obtain 1.136 g of the title compound as colorless crystal.

$^1$H—NMR (DMSO-d, δ ppm): 2.61 (4H, t, J=7.4 Hz), 2.97 (4H, t, J=7.4 Hz), 7.37 (2H, dd, J=1.5, 8.4 Hz), 7.66 (2H, brs), 7.75 (2H, d, J=8.4 Hz), 12.13 (2H, brs).

REFERENCE EXAMPLE 59

2,6-Bis(3-hydroxypropyl)naphthalene

First, 1.10 g of 2,6-bis(2-carboxyethyl)naphthalene was suspended in 8 ml of ethanol, and after adding dropwise 0.4 ml of concentrated sulfuric acid, the mixture was refluxed for 6 hours and cooled. After adding 30 ml of ice-water and 50 ml of ethyl acetate, the mixture was adjusted to pH 8.0 with 10% sodium hydroxide. The separated aqueous layer was extracted with 50 ml of ethyl acetate. The ethyl acetate layers were combined, washed with a saturated sodium chloride aqueous solution, dried over magnesium sulfate, filtered and evaporated under a reduced pressure. The residue was applied to a silica gel column and eluted with hexane/chloroform (1:1) to obtain the diethyl ester compound as a colorless crystal. To a suspension of 120 mg of lithium aluminium hydride in 5 ml of absolute tetrahydrofuran was added dropwise a solution of the above-obtained crystal in 10 ml of absolute tetrahydrofuran over 3 minutes, and the mixture was refluxed for 80 minutes. After cooling, to the reaction mixture were successively added 0.12 ml of water, 0.12 ml of 15% sodium hydroxide and 0.36 ml of water. The mixture was stirred at a room temperature for 1.5 hours, filtered, and evaporated under a reduced pressure to obtain 429 mg of the title compound as a colorless crystal.

$^1$H—NMR (CDCl$_3$, δ ppm): 1.45 (2H, brs), 1.9-2.1 (4H, m), 2.86 (4H, t, J=7.7 Hz), 3.71 (4H, t, J=6.3 Hz), 7.32 (2H, dd, J=1.5, 8.3 Hz), 7.60 (2H, brs), 7.71 (2H, d, J=8.3 Hz).

REFERENCE EXAMPLE 60

2,6-Bis(3-dimethylaminopropyl)naphthalene

To 420 mg of 2,6-bis(3-hydroxypropyl)naphthalene was added 133 μl of phosphorus tribromide, and the mixture was stirred at 80° C. for 2 hours and cooled. After adding 10 ml of ice-water, the mixture was extracted with 50 ml of ethyl acetate. The extract was washed with 5% sodium bicarbonate aqueous solution, water and a saturated sodium chloride aqueous solution, dried over magnesium sulfate, filtered and evaporated under a reduced pressure. The residue was applied to a silica gel column and eluted with hexane/benzene (10:1) to obtain 314 mg of 2,6-bis(3-bromopropyl)naphthalene as a colorless crystal.

$^1$H—NMR (CDCl$_3$, δ ppm): 2.2-2.3 (4H, m), 2.93 (4H, t, J=7.3 Hz), 3.42 (4H, t, J=6.6 Hz), 7.32 (2H, dd, J=1.6, 8.3 Hz), 7.61 (2H, brs), 7.73 (2H, d, J=8.3 Hz).

To a suspension of 150 mg of the above crystal in 1 ml of ethanol was added 424 μl of 50% dimethylamine, and the mixture was stirred at a room temperature for 24 hours to obtain a pale yellow solution. The solution was evaporated under a reduced pressure to remove the ethanol, and after adding 20 ml of water, the mixture was extracted with 50 ml of benzene. The extract was washed with a saturated sodium chloride aqueous solution, dried over magnesium sulfate, filtered and evaporated under a reduced pressure to obtain 98 mg of the title compound as a colorless crystal.

$^1$H—NMR (CDCl$_3$, δ ppm): 1.8–2.0 (4H, m), 2.23 (12H, s), 2.32 (4H, brt), 2.78 (4H, t, J=7.6 Hz), 7.31 (2H, dd, J=1.5, 8.3 Hz), 7.58 (2H, brs), 7.70 (2H, d, J=8.3 Hz).

EXAMPLE 31

2,6-Bis(3-trimethylammoniopropyl)naphthalene diiodide

First, 98 mg of 2,6-bis(3-dimethylaminopropyl)naphthalene was dissolved in 1 ml of absolute methanol, and after adding 205 μl of methyl iodide with ice-cooling and stirring, the mixture was stirred at a room temperature for 2 hours and refluxed for 30 minutes. After cooling and adding 3 ml of acetone, the reaction mixture was stirred for 5 minutes. The resulting crystal was collected by filtration, washed with acetone and dried under a reduced pressure to obtain 117 mg of the title compound as a colorless crystal.

Melting point: above 270° C.; $^1$H—NMR (D$_2$O, δ ppm): 2.2–2.4 (4H, m), 2.91 (4H, t, J=7.2 Hz), 3.08 (18H, s), 3.3–3.4 (4H, m), 7.50 (2H, brd), 7.79 (2H, brd), 7.90 (2H, d, J=8.1 Hz).

REFERENCE EXAMPLE 61

2,6-Bis(3-diethylaminopropyl)naphthalene

To a solution of 132 mg of 2,6-bis(3-bromopropyl)naphthalene in 1 ml of absolute ethanol was added dropwise 368 μl of diethylamine at a room temperature with stirring, and the mixture was refluxed for 2.5 hours and then cooled. The reaction mixture was evaporated under a reduced pressure, and after adding 20 ml of water, extracted with 50 ml of benzene. The extract was washed with a saturated sodium chloride aqueous solution, dried over magnesium sulfate, filtered, and evaporated under a reduced pressure to obtain 78 mg of the title compound as a pale yellow liquid.

$^1$H—NMR (CDCl$_3$, δ ppm): 1.01 (12H, t, J=7.1 Hz), 1.8–2.0 (4H, m), 2.49 (4H, brt), 2.53 (8H, q, J=7.1 Hz), 2.76 (4H, t, J=7.6 Hz), 7.30 (2H, dd, J=1.5, 8.3 Hz), 7.58 (2H, brs), 7.69 (2H, d, J=8.3 Hz).

EXAMPLE 32

2,6-Bis(3-triethylammoniopropyl)naphthalene diiodide

To a solution of 78 mg of 2,6-bis(3-diethylaminopropyl)naphthalene in 1 ml of absolute ethanol was added 176 μl of ethyl iodide, and the mixture was refluxed for 140 minutes and cooled. After adding 2 ml of acetone, the mixture was stirred for 20 minutes. The resulting crystal was collected by filtration, washed with acetone and dried under a reduced pressure to obtain 117 mg of the title compound as a colorless crystal.

Melting point: 248° C.–250° C. (decomposed); $^1$H—NMR (D$_2$O, δ ppm): 1.15 (18H, brt), 2.0–2.2 (4H, m), 2.91 (4H, brt), 3.1–3.3 (16H, m), 7.50 (2H, brd), 7.79 (2H, brs), 7.90 (2H, d, J=8.3 Hz).

REFERENCE EXAMPLE 62

2-(5-Bromopentyloxy)tetrahydropyran

To 31.2 g of 1,5-pentanediol was added 380 mg of p-toluenesulfonic acid monohydride and dropwise 8.4 g of dihydropyran with ice-cooling and stirring over 20 minutes, and the mixture was stirred at a room temperature for 3.5 hours. After adding 300 ml of chloroform, the mixture was washed with 2% sodium bicarbonate aqueous solution, water and a saturated sodium chloride aqueous solution, dried over magnesium sulfate, filtered and evaporated under a reduced pressure. The residue was applied to a silica gel column and eluted with hexane/ethyl acetate (3:1) to obtain 6.0 g of 2-(5-hydroxypentyloxy)tetrahydropyran as a colorless liquid.

To a solution of 1.88 g of the colorless liquid, 1.62 ml of pyridine and 6.64 g of tetrabromomethane in 20 ml of absolute ethyl ether was added at once 5.25 g of triphenylphosphine with ice-cooling and stirring, and the mixture was stirred with ice-cooling for 5 minutes and then at a room temperature overnight. After adding 20 ml of ethyl ether, the mixture was stirred, filtered to remove the resulting insoluble matter and washed with 100 ml of ethyl ether. The ethyl ether layers were combined, washed with water and a saturated sodium chloride aqueous solution, dried over magnesium sulfate, filtered and evaporated under a reduced pressure. The residue was applied to a silica gel column, eluted with hexane/ethyl acetate (20:1) to obtain 2.32 g of the title compound as a colorless liquid.

$^1$H—NMR (CDCl$_3$, δ ppm): 1.4–1.7 (10H, m), 1.7–2.0 (2H, m), 3.3–3.6 (2H, m), 3.42 (2H, t, J=6.7 Hz), 3.7–4.0 (2H, m), 4.57 (1H, brs).

REFERENCE EXAMPLE 63

1,4-Bis(5-hydroxypentylthio)benzene

A solution of 169 mg of metallic sodium in 5 ml of absolute ethanol was evaporated under a reduced pressure to remove the ethanol. Resulting sodium ethoxide was dissolved in 17.5 ml of absolute hexamethylphosphoric triamide, and to the mixture was added 497 mg of 1,4-benzenedithiol with ice-cooling and stirring and then dropwise 2.20 g of 2-(5-bromopentyloxy)tetrahydropyran over 2 minutes. The mixture was stirred at a room temperature overnight, poured into 200 ml of ice-water, saturated with sodium chloride and extracted twice with 100 ml of ethyl ether. The ethyl ether extracts were combined, washed with a saturated sodium chloride aqueous solution, dried over magnesium sulfate, filtered and evaporated under a reduced pressure. The resulting residue was applied to a silica gel column and eluted with hexane/ethyl acetate (20:3) to obtain 1.02 g of 1,4-bis[5-(2-tetrahydropyranyloxy)pentylthio]benzene as a pale yellow liquid.

To a suspension of this product in 6 ml of methanol was added 10 mg of p-toluenesulfonic acid monohydride at a room temperature with stirring, and the mixture was stirred for 3 hours. After adding 50 ml of chloroform, the mixture was washed with 5% sodium bicarbonate aqueous solution and a saturated sodium chloride aqueous solution, dried over magnesium sulfate, filtered and evaporated under a reduced pressure to obtain 642 mg of the title compound as a colorless crystal.

$^1$H—NMR (CDCl$_3$, δ ppm): 1.4–1.8 (14H, m), 2.90 (4H, t, J=7.1 Hz), 3.60 (4H, brt), 7.24 (4H, s).

REFERENCE EXAMPLE 64

1,4-Bis(5-dimethylaminopentylthio)benzene

To 640 mg of 1,4-bis(5-hydroxypentylthio)benzene was added 157 μl of phosphorus tribromide with ice-cooling and stirring, and the mixture was stirred at a room temperature for 10 minutes and then at 80° C. for an hour. After cooling and adding 20 ml of ice-water, the mixture was extracted with 50 ml of ethyl acetate.

The extract was washed with a saturated sodium chloride aqueous solution, dried over magnesium sulfate, filtered and evaporated under a reduced pressure. The residue was applied to a silica gel column and eluted with hexane/ethyl acetate (50:1) to obtain 533 mg of 1,4-bis(5-bromopentylthio)benzene as a colorless crystal.

To a solution of this crystal in 3 ml of absolute ethanol was added 1.25 ml of diethylamine, and the mixture was refluxed for 2 hours and stirred at a room temperature overnight. After adding 15 ml of 5% sodium bicarbonate aqueous solution, the mixture was extracted with 50 ml of benzene. The extract was washed with a saturated sodium chloride aqueous solution, dried over magnesium sulfate and filtered, and evaporated under a reduced pressure to obtain 510 mg of the title compound as a pale reddish liquid.

$^1$H—NMR (CDCl$_3$, δ ppm): 1.01 (12H, t, J=7.1 Hz), 1.45 (8H, brs), 1.5–1.7 (4H, m), 2.40(4H, brt), 2.50 (8H, q, J=7.1 Hz), 2.89 (4H, t, J=7.3 Hz), 7.23 (4H, s).

EXAMPLE 33

1,4-Bis(5-triethylammoniopentylthio)benzene diiodide

First, 510 mg of 1,4-bis(5-diethylaminopentylthio)benzene was dissolved in 5 ml of absolute ethanol, and after adding 960 μl of ethyl iodide, the mixture was refluxed for 4 hours, then cooled and evaporated under a reduced pressure to remove the ethanol. After adding 5 ml of acetone, the mixture was stirred at a room temperature for 3 hours and allowed to stand in a freezer overnight. The resulting crystal was collected by filtration, washed with acetone and dried under a reduced pressure to obtain 519 mg of the title compound as a light gray crystal.

$^1$H—NMR (D$_2$O, δ ppm): 1.24 (18H, brt), 1.4–1.6 (4H, m), 1.6–1.8 (8H, m), 2.9–3.2 (8H, m), 3.24 (12H, brq), 7.36 (4H, s).

REFERENCE EXAMPLE 65

4,4'-Bis(3-hydroxypropyl)biphenyl

To a solution of 9.20 g of 4,4'-diiodobiphenyl and 2.47 g of propargyl alcohol in 90 ml of triethylamine, were added 140 mg of di(triphenylphosphine).palladium dichloride and 76 mg of cuprous iodide at a room temperature, and the mixture was stirred for 24 hours. After adding additional 0.90 g of propargyl alcohol, the mixture was stirred for further 6 hours, poured into water, adjusted to pH 6 with 6N hydrochloric acid and extracted three times with 200 ml of tetrahydrofuran. The extract was dried over magnesium sulfate and concentrated under a reduced pressure. The concentrate was applied to a silica gel column and eluted with chloroform/methanol (20:1) to obtain 4.5 g of 4,4'-bis(3-hydroxy-1-propynyl)biphenyl as a brown crystal.

$^1$H—NMR (DMSO-d6, δ ppm): 4.33 (4H, d, J=6.1 Hz), 5.36 (2H, t, J=6.1 Hz), 7.52 (4H, d, J=8.3 Hz), 7.72 (4H, d, J=8.3 Hz).

To a solution of 2.32 g crystal thus obtained in 200 ml of 1,4-dioxane was added 2.3 g of 5% palladium on carbon, and the mixture was stirred under hydrogen flow at a room temperature for 1.5 hours. The reaction mixture was filtered to remove the catalyst, and evaporated to dryness under a reduced pressure to obtain 2.09 g of the title compound as a pale gray powder.

$^1$H—NMR (DMSO-d6, δ ppm): 1.6–1.8 (4H, m), 2.64 (4H, t, J=7.6 Hz), 3.43 (4H, dd, J=6.4, 5.1 Hz), 4.49 (2H, t, J=5.1 Hz), 7.26 (4H, d, J=8.3 Hz), 7.54 (4H, d, J=8.3 Hz).

REFERENCE EXAMPLE 66

4,4'-Bis(3-dimethylaminopropyl)biphenyl

To 2.09 g of 4,4'-bis(3-hydroxypropyl)biphenyl was added 0.60 ml phosphorus tribromide at a room temperature, and the mixture was stirred for 2 hours at 80° C., poured into a saturated sodium bicarbonate aqueous solution, and extracted with 100 ml of chloroform and three times with 100 ml of chloroform/tetrahydrofuran (1:1). The extract was dried over magnesium sulfate and concentrated under a reduced pressure. The resulting residue was applied to a silica gel column and eluted with hexane/benzene (20:1) to obtain 2.09 g of 4,4'-bis(3-bromopropyl)diphenyl as colorless crystal.

$^1$H—NMR (CDCl$_3$, δ ppm): 2.1–2.3 (4H, m), 2.82 (4H, t, J=7.3 Hz), 3.43 (4H, t, J=6.7 Hz), 7.26 (4H, d, J=8.3 Hz), 7.51 (4H, d, J=8.3 Hz).

To a solution of 515 mg of the crystal thus obtained in 4 ml of ethanol was added 0.68 ml of 50% aqueous dimethylamine solution at a room temperature, and the mixture was stirred for 2 hours. After adding 6 ml of tetrahydrofuran, the mixture was stirred for an hour. After further adding 0.68 ml of 50% aqueous dimethylamine solution, the mixture was stirred for 20 hours. After further addition of 0.68 ml of 50% dimethylamine aqueous solution, the mixture was stirred at 80° C. for 2 hours in the reaction flask equipped with a gum balloon. After cooling, the reaction mixture was concentrated under a reduced pressure, 5% sodium bicarbonate aqueous solution was added, and the mixture was extracted three times with 50 ml of benzene. The extract was washed with 5% sodium bicarbonate aqueous solution and a saturated sodium chloride aqueous solution, dried over magnesium sulfate, concentrated to dryness under a reduced pressure and dried in vacuo to obtain 340 mg of the title compound as a colorless oil.

$^1$H—NMR (CDCl$_3$, δ ppm): 1.7–1.9 (4H, m), 2.24 (12H, s), 2.32 (4H, t, J=7.4 Hz), 2.67 (4H, t, J=7.8 Hz), 7.25 (4H, d, J=8.3 Hz), 7.50 (4H, d, J=8.3 Hz).

EXAMPLE 34

4,4'-Bis(3-trimethylammoniopropyl)biphenyl diiodide

To a solution of 340 mg of 4,4'-bis(3-dimethylaminopropyl)biphenyl in 3 ml of methanol was added 0.65 ml of methyl iodide, and the mixture was stirred under nitrogen flow in dark at a room temperature for 2 hours, refluxed for an hour, allowed to be cooled, and cooled in a freezer for an hour. The resulting crystal was collected by filtration, washed with methanol, acetone and n-hexane, and dried under a reduced pressure to obtain the primary crystal. The filtrate was treated as described above to obtain the secondary crystal. The crystals were combined and recrystallized from 1 ml of methanol, washed with methanol, acetone and n-hexane, and dried under a reduced pressure to obtained 393 mg of the title compound as a colorless crystal.

Melting point: 252° C.–254° C.;

$^1$H—NMR (D$_2$O, δ ppm): 2.1–2.3 (4H, m), 2.80 (4H, t, J=7.3 Hz), 3.10 (18H, s), 3.3–3.4 (4H, m), 7.43 (4H, d, J=8.3 Hz), 7.69 (4H, d, J=8.3 Hz).

REFERENCE EXAMPLE 67

4,4'-Bis(3-diethylaminopropyl)biphenyl

A solution of 515 mg of 4,4'-bis(3-bromopropyl)biphenyl and 0.95 g of diethylamine in 1.3 ml of ethanol was refluxed in a flask equipped with a balloon for 2 hours, cooled, and concentrated under a reduced pressure. To the concentrate was added 5% sodium bicarbonate aqueous solution, the mixture was extracted three times with 50 ml benzene. The extract was washed with 5% sodium bicarbonate aqueous solution and a saturated sodium chloride aqueous solution, dried over magnesium sulfate, concentrated under a reduced pressure to and dried in vacuo obtain 420 mg of the title compound as a yellow oil.

$^1$H—NMR (CDCl$_3$, δ ppm): 1.02 (12H, t, J=7.1 Hz), 1.7-1.9 (4H, m), 2.4-2.7 (16H, m), 7.25 (4H, d, J=8.3 Hz), 7.50 (4H, d, J=8.3 Hz).

EXAMPLE 35.

4,4'-Bis(3-triethylammoniopropyl)biphenyl diiodide

To a solution of 400 mg of 4,4'-bis(3-diethylaminopropyl)biphenyl in 4 ml of ethanol was added 0.84 ml of ethyl iodide, and the mixture was refluxed for 3 hours. After adding further 0.42 ml of methyl iodide, the mixture was refluxed for 2 hours and concentrated under a reduced pressure. To the concentrate were added 5 ml of acetone and 50 ml of ethyl acetate. The resulting crystal was collected by filtration, washed with ethanol, acetone and n-hexane, and dried under a reduced pressure. The obtained pale yellow powder was recrystallized from 10 ml of ethanol to obtain 475 mg of the title compound as a pale yellow crystal.

Melting point: 260° C.-262° C.;

$^1$H—NMR (D$_2$O, δ ppm): 1.1-1.3 (18H, m), 1.9-2.1 (4H, m), 2.78 (4H, t, J=6.8 Hz), 3.1-3.3 (16H, m), 7.43 (4H, d, J=8.3 Hz), 7.69 (4H, d, J=8.3 Hz).

REFERENCE EXAMPLE 68.

7-Octyn-1-ol

To a solution of 14.3-7g of 6 chloro-1-hexanol and 10.39 g of dihydropyran in 30 ml of methylene chloride was added 0.95 g of tosic acid monohydrate, and the mixture was stirred at room temperature for 18 hours, poured into 50 ml of a saturated sodium bicarbonate aqueous solution, stirred for 10 minutes and extracted three times with 100 ml of chloroform. The extracts were combined, washed with a saturated sodium bicarbonate aqueous solution and a saturated sodium chloride aqueous solution, dried over magnesium sulfate, concentrated under a reduced pressure and dried in vacuo. The orange-colored oil thus obtained was vacuum-distilled to obtain 17.43 g of 2-(6-chlorohexyloxy)tetrahydropyran as a colorless oil.

Boiling point 108° C.-110° C. (2 mmHg);

$^1$H—NMR(CDCl$_3$, δ ppm): 1.2-1.9 (14H, m), 3.3-4.0 (6H, m), 4.58 (1H, brs).

To a solution of 6.8 g of lithium acetylydeethylenediamine complex in 30 ml of dimethyl sulfoxide was added dropwise a solution of 11.03 g of the above-obtained colorless oil in 10 ml of dimethyl sulfoxide over 20 minutes under nitrogen flow at a room temperature, and the mixture was stirred for 4 hours, poured into ice-water, salted out with sodium chloride, and extracted three times with 100 ml of ethyl ether. The extracts were combined, dried over magnesium sulfate, concentrated under a reduced pressure and dried in vacuo to obtain 9.46 g of 2-(7-octynyloxy)tetrahydropyran as a yellow oil.

$^1$H—NMR (CDCl$_3$, δ ppm): 1.2-2.3 (17H, m), 3.3-4.0 (4H, m), 4.57 (1H, brs).

To a solution of 9.46 g of the oil thus obtained in 20 ml of methanol was added 0.5 g of tosic acid monohydrate, and the mixture was stirred for 19 hours at a room temperature. After adding water, the reaction mixture was extracted three times with 100 ml of ethyl acetate. The combined extract was washed with a saturated sodium chloride aqueous solution, dried over magnesium sulfate, concentrated under a reduced pressure and dried in vacuo. The resulting yellow oil was vacuum-distilled to obtain 4.18 g of the title compound as a colorless oil.

Boiling point: 78° C.-80° C. (2 mmHg);

$^1$H—NMR (CDCl$_3$, δ ppm): 1.2-2.3 (11H, m), 3.65 (2H, t, J=7.6 Hz).

REFERENCE EXAMPLE 69

1,4-Bis(8-hydroxyoctyl)benzene

A solution of 3.30 g of 1,4-iodobenzene, 2.77 g of 7-octyn-1-ol, 70 mg of di(triphenylphosphine).palladium dichloride and 38 mg of cuprous iodide in 40 ml of triethylamine was stirred at a room temperature for 17 hours. After adding further 0.50 g of 7-octyn-1-ol, 70 mg of di(triphenylphosphine).palladium dichloride and 40 mg of cuprous iodide, the reaction mixture was stirred for 24 hours. After adding further 0.50 g of 7-octyn-1-ol, the mixture was stirred for 5 hours; after adding 170 mg of cuprous iodide, the mixture was stirred for 2.5 hours; and finally after adding 0.2 g of 7-octyn-1-ol and 130 mg of di(triphenylphosphine). palladium dichloride the reaction mixture was stirred for 18 hours. The reaction mixture was filtered to remove insoluble matter, concentrated under a reduced pressure, and after adding water, extracted three times with 100 ml of ethyl acetate. The extract was washed with a saturated sodium chloride aqueous solution, dried over magnesium sulfate, concentrated under a reduced pressure. The residue was applied to a silica gel column and eluted with chloroform/methanol (100:1 to 50:1) to obtain 1.39 g of 1,4-bis(8-hydroxy-1-octynyl)benzene as a light brown powder.

$^1$H—NMR(CDCl$_3$, δ ppm): 1.2-1.7 (16H, m), 2.41 (4H, t, J=6.8 Hz), 3.66 (4H, q, J=6.4 Hz), 7.29 (4H, s).

To a solution of 1.93 g of 1,4-bis(8-hydroxy-1-octynyl)benzene obtained above in 100 ml of methanol was added 0.56 g of 5% palladium on carbon, and the mixture was reacted under hydrogen flow for an hour and filtered to remove the catalyst. The filtrate was concentrated under a reduced pressure to and dried in vacuo obtain 1.84 g of the title compound as a colorless crystal.

$^1$H—NMR (DMSO-d, δ ppm): 1.1-1.6 (24H, m), 2.4-2.6 (4H, m), 3.1-3.3 (4H, m), 4.32 (2H, brt), 7.06 (4H, s).

REFERENCE EXAMPLE 70

1,4-Bis(8-diethylaminooctyl)benzene

To 1.84 g of 1,4-bis(8-hydroxyoctyl)benzene was added 0.42 ml of phosphorus tribromide, the mixture was stirred at 80° C. for 2.5 hours, poured into ice-water, and extracted three times with 50 ml of ethyl acetate. The extracts were combined, washed with a saturated sodium chloride aqueous solution, dried magnesium sulfate, and concentrated under a reduced pressure. The residue was applied to a silica gel column and eluted with n-hexane/benzene (20:1) to obtain 2.13 g of 1,4-bis(8-bromooctyl)benzene as a colorless crystal.

$^1$H—NMR(CDCl$_3$, δ ppm): 1.2-1.9 (24H, m), 2.56 (4H, t, J=7.5 Hz), 3.40 (4H, t, J=6.8 Hz), 7.08 (4H, s).

A solution of 924 mg of the crystal above obtained and 1.46 g of diethylamine in 2 ml of ethanol was refluxed for 3.5 hours, cooled and concentrated under a reduced pressure. After adding 5% sodium bicarbonate aqueous solution, the mixture was extracted three times with 100 ml of benzene. The extract was washed with 5% sodium bicarbonate aqueous solution and a saturated sodium chloride aqueous solution, dried over magnesium sulfate, concentrated under a reduced pressure and dried in vacuo to obtain 820 mg of the title compound as a yellow oil.

$^1$H—NMR (CDCl$_3$, δ ppm): 1.03 (12H, t, J=7.3 Hz), 1.1-1.7 (24H, m), 2.41 (4H, t, J=7.5 Hz), 2.53 (4H, brt), 2.53 (8H, q, J=7.3 Hz), 7.08 (4H, s).

EXAMPLE 36

1,4-Bis(8-triethylammoniooctyl)benzene diiodide

To a solution of 223 mg of 1,4-bis(8-diethylaminooctyl)benzene in 1 ml of ethanol was added 0.40 ml of ethyl iodide, and the mixture was refluxed for 2 hours, concentrated under a reduced pressure and further dried under reduced pressure. To the residue was added 3 ml of ethyl acetate to solidify the residue. To the solid was added 3 ml of acetone and the whole was stirred for 10 minutes and filtered. The resulting crystal was washed with ethyl acetate and n-hexane, and dried under a reduced pressure to obtain 315 mg of the title compound as a yellow crystal.

Melting points: 122° C.-127° C.;

$^1$H—NMR (D$_2$O, δ ppm): 1.1-1.7 (42H, m), 2.52 (4H, brt), 3.0-3.4 (16H, m), 7.07 (4H, s).

REFERENCE EXAMPLE 71

2,2'-Ethylenebis[2-(3-dimethylaminopropyl)-m-dithian]

Under nitrogen flow 2.66 g of 2,2 -ethylenebis(m-dithian) was suspended in 70 ml of absolute tetrahydrofuran, and after adding dropwise 7.69 ml of 1.6M n-butyl lithium in n-hexane while stirring at −28° C. to −23° C. over 10 minutes, the mixture was stirred at the same temperature for 1.5 hours. After adding dropwise 1.46 g of 3-dimethylaminopropyl chloride at −5° C. to −3° C. over 5 minutes, the mixture was stirred with ice-cooling for an hour. The reaction mixture was again cooled to −28° C., and after adding the same amount of n-butyl lithium and 3-dimethylaminopropyl chloride as described above, further stirred overnight at a room temperature with stirring.

The pale yellow liquid thus obtained was ice-cooled, and after adding 30 ml of ice-water, the tetrahydrofuran was evaporated under a reduced pressure, and the mixture was extracted with 100 ml and 50 ml of chloroform. The extracts were combined, washed with a saturated sodium chloride aqueous solution, dried over magnesium sulfate, filtered and evaporated under a reduced pressure. The residue was applied to a silica gel column and eluted with chloroform/methanol/triethylamine (100:50:1) to obtain 1.03 g of the title compound as a pale yellow liquid.

$^1$H—NMR (CDCl$_3$, δ ppm): 1.6-1.8 (8H, m), 1.8-2.1 (8H, m), 2.22 (12H, s), 2.2-2.3 (4H, brt), 2.7-3.0 (8H, m).

REFERENCE EXAMPLE 72

1,10-Bis(dimethylamino)-4,7-decanedione

First, 695 mg of 2,2'-ethylenebis[2-(3-dimethylaminopropyl)-m-dithian] was dissolved in 24 ml of absolute methanol and 6 ml of absolute tetrahydrofuran, and after adding dropwise a solution of 3.12 g of thallium (III) nitrate trihydrate in 18 ml of absolute methanol over 2 minutes while stirring at a room temperature, the mixture was stirred for 30 minutes, filtered to remove insoluble matter, and evaporated under a reduced pressure to remove the solvent. After adding 30 ml of water, the mixture was extracted with 100 ml and 50 ml of chloroform. The extracts were combined, washed with a saturated sodium chloride aqueous solution, dried over magnesium sulfate, filtered, and evaporated under a reduced pressure. The residue was applied to a silica gel column and eluted with chloroform/methanol/triethylamine (80:20:1) to obtain 178 mg of the title compound as a pale yellow liquid.

EI Mass m/z: 256 (M+);

$^1$H—NMR (CDCl$_3$, δ ppm): 1.6-1.8 (4H, m), 2.20 (12H, s), 2.25 (4H, brt), 2.50 (4H, t, J=7.3 Hz), 2.69 (4H, s).

EXAMPLE 37

4,7-Dioxodecamethylenebis(trimethylammonium) diiodide

To a solution of 79 mg of 1,10-bis(dimethylamino)-4,7-decanedione in 0.8 ml of absolute methanol was added 192 μl of methyl iodide with stirring at a room temperature, and the mixture was stirred for 3 hours, refluxed for 20 minutes. After adding 2 ml of acetone with heating, the reaction mixture was allowed to stand with stirring overnight in a freezer. Next, the resulting crystal was collected by filtration, washed with acetone, and dried over a reduced pressure to obtain 140 mg of the title compound as a colorless crystal.

Melting point: 180° C.-182° C.;

$^1$H—NMR (D$_2$O, δ ppm): 1.9-2.1 (4H, m), 2.72 (4H, t, J=2.7 Hz), 2.81 (4H, s), 3.12 (18H, s), 3.2-3.4 (4H, m).

REFERENCE EXAMPLE 73

1,10-Bis(dimethylamino)-4,7-decanediol

To a solution of 95 mg of 1,10-bis(dimethylamino)-4,7-decanedione in 3 ml of methanol was added 36 mg of sodium borohydride with ice-cooling, and the mixture was stirred for an hour, and after adding 5 ml of acetone, concentrated under a reduced pressure. After adding chloroform, the mixture was again concentrated under reduced pressure. After adding 5 ml of chloroform, the mixture was filtered to remove insoluble matter, concentrated under a reduced pressure, and further dried under a reduced pressure to obtain 79 mg of the title compound comprising Syn/Anti (1:1) mixture as a yellow oil.

$^1$H—NMR (CDCl$_3$, δ ppm): 1.3-2.4 (28H, m), 3.51 (2H, brs), 7.14 (1H, brs), 7.26 (1H, brs).

EXAMPLE 38

4,7-Dihydroxydecamethylenebis(trimethylammonium) diiodide

To a solution of 79 mg of 1,10-bis(dimethylamino)-4,7-decanediol in 1 ml of methanol was added 0.2 ml of methyl iodide, and the mixture was stirred at a room temperature in dark for 3 hours, and then refluxed for 1.5 hours. The reaction mixture was concentrated to dryness under a reduced pressure, dried in vacuo, and solidified with 10 ml of ethyl acetate. The colorless powder was collected by filtration, dissolved in 0.5 ml of methanol and 0.5 ml of acetone, and concentrated under a reduced pressure and dried in vacuo to obtain 42 mg of the title compound comprising Syn/Ant mixture as a colorless crystal.

Melting point: 206° C.-208° C.;

$^1$H—NMR (D$_2$O, δ ppm): 1.4–2.0 (12H, m), 3.12 (18H, s), 3.34 (4H, t, J=8.5 Hz), 3.70 (2H, brs).

REFERENCE EXAMPLE 74

Ethyl p-(4-bromobutyl)benzoate

To 50 ml of triethylamine were added 5.52 g of ethyl p-iodobenzoate, 1.54 g of 3-butyn-1-ol, 41 mg of cuprous iodide and 77 mg of bis(triphenylphosphine) palladium chloride, and the mixture was stirred for 2.5 hours under nitrogen flow. After adding 50 ml of ethyl acetate, the mixture was filtered to remove the precipitate, washed three times with 30 ml of water, dried over magnesium sulfate, and evaporated under a reduced pressure to obtain 4.4 g of ethyl p-(4-hydroxy-1-butynyl)benzoate as a colorless oil.

Next, 4.4 g of the oil obtained above was stirred together with 1.2 g of 5% palladium on carbon in 50 ml of methanol under a hydrogen atmosphere to obtain 4.3 g of ethyl p-(4-hydroxybutyl)benzoate. To this product was added 2.0 g of phosphorus tribromide with ice-cooling, and the mixture was heated at 80° C. for 1.5 hours. The reaction mixture was poured into 50 ml of ice-water, and extracted twice with 50 ml of ethyl acetate. The extract was dried over magnesium sulfate, evaporated under a reduced pressure. The residue was applied to a silica gel column and eluted with chloroform/hexane (1:1) to obtain 5.0 g of the title compound as a colorless oil.

$^1$H—NMR (CDCl$_3$, δ ppm): 1.38 (3H, t, J=7.1 Hz), 1.85 (4H, m), 2.69 (2H, t, J=7.1 Hz), 3.41 (2H, t, J=6.4 Hz), 4.36 (2H, q, J=7.1 Hz), 7.25 (2H, d, J=8.3 Hz), 7.98 (2H, d, J=8.3 Hz).

EXAMPLE 39

2-Dimethylaminoethyl p-(4-dimethylaminobutyl)benzoate bis(methyl iodide)

First, 4.2 g of the oil obtained in Reference Example 74 was dissolved in 30 ml of ethanol, and after adding 26 ml of 50% aqueous dimethyl amine solution the mixture was stirred at a room temperature for 4 hours, concentrated under a reduced pressure. After adding 50 ml of water, the mixture was extracted three times with 20 ml of ethyl acetate. The extract was dried over magnesium sulfate and evaporated under a reduced pressure to obtain 3.0 g of ethyl p-(4-dimethylaminobutyl)benzoate.

To 2.68 g of this compound was added 10.7 ml of 1N sodium hydroxide, and the mixture was stirred at 70° C. for 12 hours, and evaporated under a reduced pressure to remove the water. The residue was dried in the presence of phosphorus pentoxide under a reduced pressure to obtain 2.58 g of a colorless powder.

1.9 g of this powder was suspended in 30 ml of dimethylformamide, and after adding 1.25 g of dimethylamino-ethylchloride the mixture was stirred at 60° C. for 4 hours. After cooling and adding 50 ml of ethyl acetate, the mixture was washed twice with 20 ml of water, dried over magnesium sulfate and evaporated under a reduced pressure to obtain 1.0 g of 2-dimethylaminoethyl p-(4-dimethylaminobutyl)benzoate. To the ester thus obtained were added 7 ml of methanol and 2.1 ml of methyl iodide, and the mixture was stirred at a room temperature overnight. The resulting crystal was collected by filtration, washed with methanol and dried under a reduced pressure to obtain 1.65 g of the title compound as a pale yellow crystal.

Melting point: 248° C. (decomposed);

IR (KBr) cm$^{-1}$: 2960, 1715, 1275. $^1$H—NMR(D$_2$O, δ ppm): 1.75 (4H, m), 2.80 (2H, brt), 3.07 (6H, s), 3.28 (6H, s), 3.10–3.40 (4H, m), 3.90 (2H, m), 7.45 (2H, d, J=8.3 Hz), 8.0 (2H, d, J=8.3 Hz).

REFERENCE EXAMPLE 75

Methyl p-(3-bromopropylthio)benzoate

To 40 ml of chloroform were added 4.0 g of methyl 4-mercaptobenzoate, 3.3 g of 3-bromo-1-propanol and 2.38 g of triethylamine, and the mixture was stirred for an hour and then evaporated under a reduced pressure. After adding 50 ml of ethyl acetate, the mixture was washed with 30 ml each of water, 1N hydrochloric acid and a saturated sodium bicarbonate aqueous solution, dried over magnesium sulfate and evaporated under a reduced pressure. The residue was applied to a silica gel column and eluted with chloroform/methanol (100:3) to obtain 3.6 g of methyl p-(3-hydroxypropylthio)benzoate as a colorless crystal. To 3.0 g of this crystal was added 1.44 g of phosphorus tribromide, and the mixture was heated at 80° C. for 2 hours, poured into 50 ml of ice-water, and extracted three times with 20 ml of ethyl acetate. The extract was dried over magnesium sulfate, and evaporated under a reduced pressure. The residue was applied to a silica gel column and eluted with chloroform/hexane (1:1) to obtain 3.0 g of the title compound as a colorless oil.

$^1$H—NMR (CDCl$_3$, δ ppm): 2.1–2.3 (2H, m), 3.15 (2H, t, J=7.0 Hz), 2.53 (2H, t, J=6.5 Hz), 3.9 (3H, s), 7.28 (2H, d, J=8.0 Hz), 7.93 (2H, d, J=8.0 Hz).

EXAMPLE 40

Dimethylaminoethyl p-(3-dimethylaminopropylthio)benzoate bis(methyl iodide)

First, 3.0 g of the oil obtained in Reference Example 75 was dissolved in 30 ml of methanol, and after adding 18 ml of 50% aqueous dimethylamine solution the mixture was stirred at a room temperature for 5 hours and then evaporated under a reduced pressure. After adding 30 ml of water, the mixture was extracted twice with 20 ml of ethyl acetate. The extract was dried over magnesium sulfate, and evaporated under a reduced pressure to obtain 2.2 g of methyl p-(3-dimethylaminopropylthio)benzoate as a colorless oil. To this oil was added 8.7 ml of 1N sodium hydroxide, and the mixture was stirred at 80° C. for 2 hours and evaporated under a reduced pressure. The residue was dried in the presence of phosphorus pentaoxide under a reduced pressure to obtain 2.4 g of sodium p-(3-dimethylaminopropylthio)benzoate as a powder. 2.0 g of this powder and 1.2 g of 2-dimethylaminoethyl chloride were added in 30 ml of dimethylformamide. The mixture was stirred at 60° C. for 4 hours and after adding 100 ml of sodium chloride aqueous solution, extracted three times with 30 ml of ethyl acetate. The extract was dried over magnesium sulfate and evaporated under a reduced pressure to obtain 1.7 g of 2-diethylaminoethyl p-(3-dimethylaminopropylthio)-benzoate as a colorless oil. To 1.0 g of this product were added 7 ml of methanol and 4.5 g methyl iodide, and the mixture was stirred at a room temperature overnight. The resulting crystal was collected by filtration to obtain 1.37 g of the title compound as a colorless crystal.

Melting point: 240° C.-242° C.;

IR (KBr) cm$^{-1}$: 1710, 1590, 1270, 1110.

$^1$H—NMR(D$_2$O, δ ppm:) 2.1-2.3 (2H, m), 3.08 (9H, s), 3.18 (4H, t, J=6.8 Hz), 3.28 (9H, s), 3.5 (2H, m), 3.9 (2H, m), 7.5 (2H, d, J=8.5 Hz), 7.98 (2H, d, J=8.5 Hz).

REFERENCE EXAMPLE 76

Methyl p-(6-bromohexyl)dihydrocinnamate

To 40 ml of triethylamine were added 3.68 g of methyl p-iododihydrocinnamate, 1.49 g of 5-hexyl-1-ol, 40 ml of cuprous iodide and 77 mg of bis(triphenylphosphine)-palladium chloride, and the mixture was stirred under nitrogen flow for 2.5 hours. After adding 50 ml of ethyl acetate, the mixture was filtered to remove the resulting precipitate, washed three-times with 30 ml of water, dried over magnesium sulfate, and evaporated under a reduced pressure to obtain 4.0 g of methyl p-(6-hydroxy-1-hexynyl)dihydrocinnamate as an oil. 4.0 g of this oil was stirred with 1.2 g of 5% palladium on carbon in 50 ml of methanol under a hydrogen atmosphere to obtain 2.41 g of methyl p-(6-hydroxyhexyl)dihydrocinnamate. To this compound was added 1.0 g of phosphorus tribromide with ice-cooling, and the mixture was heated at 80° C. for 2 hours, poured into 50 ml of ice-water. The mixture was extracted twice with 50 ml of ethyl acetate, dried over magnesium sulfate and evaporated under a reduced pressure to obtain a residue, which was then applied to a silica gel column and eluted with chloroform/hexane (1:1) to obtain 2.1 g of the title compound as a colorless oil.

$^1$H—NMR (CDCl$_3$, δ ppm): 1.2-1.7 (6H, m), 1.8-1.9 (2H, m), 2.5-2.7 (4H, m), 2.92 (2H, t, J=7.0 Hz), 3.4 (2H, t, J=7.0 Hz), 3.67 (3H, s), 7.1 (4H, s).

EXAMPLE 41

2-Diethylaminoethyl p-(6-diethylaminohexyl)dihydrocinnamate bis(ethyl iodide)

To 10 ml of methanol was added 2.1 g of methyl p-(6-bromohexyl)dihydrocinnamate and 4.67 g of diethylamine, and the mixture was refluxed for 5 hours. The solvent was evaporated off under a reduced pressure, 50 ml of ethyl acetate was added to the residue, and the mixture was washed twice with 20 ml of water, dried over magnesium sulfate and evaporated under a reduced pressure, to obtain 1.73 g of methyl p-(6-diethylaminohexyl)dihydrocinnamate as a colorless oil. To 1.5 g of this oil was added 4.7 ml of 1N sodium hydroxide aqueous solution, the mixture was stirred with heating at 85° C. for 3 hours, and water was evaporated off under a reduced pressure to obtain a residue, which was then dried in the presence of phosphorus pentaoxide under a reduced pressure to obtain 1.5 g of sodium p-(6-diethylaminohexyl)dihydrocinnamate. To 20 ml of dimethylformamide were added 1.4 g of the above salt and 0.86 g of diethylaminoethylchloride, and the reaction mixture was stirred for 4 hours at 60° C. After adding 50 ml of a saturated sodium chloride aqueous solution, the reaction mixture was extracted three times with 20 ml of ethyl acetate, and the extract was washed three times with water, dried over magnesium sulfate and evaporated under a reduced pressure to obtain 1.43 g of 2-diethylaminoethyl p-(6-diethylaminohexyl)dihydrocinnamate as a residue. Next, 1 g of this compound and 6 ml of ethyl iodide were added to 7 ml of ethanol, and the mixture was refluxed for 8 hours and allowed to stand in a freezer. The resulting crystal was recovered by filtration, washed twice with 10 ml of ethanol, and dried in the presence of phosphorus pentaoxide under a reduced pressure to obtain 0.8 g of the title compound as a colorless crystal.

Melting point: 131° C. to 133° C.;

IR (KBr) cm$^{-1}$: 2960, 1730, 1450, 1240;

$^1$H—NMR (D$_2$O, δ ppm): 1.15-1.30 (18H, m), 1.3-1.45 (4H, m), 1.50-1.70 (4H, m), 2.64 (2H, t, J=7.8 Hz), 2.75 (2H, brt, J=6.1 Hz), 2.93 (2H, brt, J=6.1 Hz), 3.0-3.3 (14H, m), 3.4-3.5 (2H, m), 4.3-4.4 (2H, m), 7.22 (4H, s).

EXAMPLE 42

1,4-Bis(6-triethylammoniohexyl)benzene dichloride

First, 2.75 g of the crystal obtained in Example 21 was dissolved in 50 ml of water, and the solution was passed through a column filled with 50 ml of Dowex 1-X8 ion exchanger resin (Bow Chemical, USA) to obtain a flow-through fraction. This fraction was concentrated under a reduced pressure and the concentrate was lyophilized to obtain 2.0 g of amorphous powder. This powder was triturated in 25 ml of acetone, and was stirred at a room temperature for 24 hours to form a crystal, which was then recovered by filtration, washed with acetone and dried under a reduced pressure to obtain 1.56 g of the title compound as a colorless crystal.

Melting point: 166° C. to 169° C. (decomposed);

NMR (D20) δ ppm: 1.22 (6H, t, J=7.3 Hz), 1.23 (6H, t, J=7.3 Hz), 1.24 (6H, t, J=7.3 Hz), 1.37 (8H, brs), 1.62 (8H, brs), 2.60 (4H, t, J=7.4 Hz), 3.10 (4H, m), 3.24 (12H, q, J=7.3 Hz), 7.22 (4H, s).

PHARMACOLOGICAL TEST

To demonstrate the usefulness of the present compounds, the muscle relaxation activity, and the muscle relaxation activity under a diabetic condition, were determined.

Muscle relaxation action IC$_{50}$)

To prepare neuromuscular preparations ddY mice 6 to 10 weeks old weighing 27.0 to 42.0 g were decapitated, venesected, and the hemiinterseptum neuromuscule was removed. This preparation was suspended by applying 1 gram of a strain in Krebs-Henseleit's solution at 36 ±1° C., through which a mixed gas of carbon dioxide/oxygen (5:95) was passed, an electric shock (0.4 to 0.5V, 0.2 Hz, 1.0 n sec.) was applied to the nerve by platinum electrodes, and the resulting short contraction reaction was detected by an isometric transducer (Nippon Koden Sha, Japan) and recorded by a biophysiograph system (San-Ei, Japan). An average of 12 contraction height data obtained one minute prior to the administration of a test compound was used as a control. The test compound was accumulatively administered at two minute intervals, and the contraction height two minutes after each administration was compared with the control, to calculate the percentage of inhibition. To ensure the reliability of the tests, usually four measurements were used for each administration. The IC$_{50}$ value was obtained on a line linearized by the method of least aqueous from a scope from a 10 to 60% inhibition in a log dose-inhibition curve.

| Example No. (*Reference Example No.) | IC$_{50}$ (90% reliance) μM | |
| --- | --- | --- |
| 1 | 22.8 | (20.0–26.0) |
| 5* | 77.7 | (70.3–86.0) |
| 2 | 26.0 | (22.3–30.0) |
| 3 | 209 | (190–228) |
| 4 | 450 | (405–499) |
| 9* | 1290 | (938–1760) |
| 5 | 556 | (481–644) |
| 6 | 176 | (160–194) |
| 7 | 119 | (103–138) |
| 8 | 207 | (177–242) |
| 9 | 31.5 | (28.1–35.3) |
| 10 | 11.2 | (9.59–13.1) |
| 11 | 60.7 | (47.8–77.2) |
| 12 | 750 | (679–829) |
| 13 | 1440 | (1370–1530) |
| 24* | 146 | (137–154) |
| 15 | 252 | (221–288) |
| 16 | 531 | (454–622) |
| 17 | 59.7 | (57.3–62.2) |
| 18 | 52.4 | (45.7–60.0) |
| 19 | 95.9 | (82.6–111) |
| 20 | 15.9 | (13.4–19.0) |
| 21 | 6.81 | (6.41–7.23) |
| 22 | 17.3 | (15.9–18.9) |
| 23 | 12.7 | (11.1–14.7) |
| 24 | 84.5 | (78.9–90.6) |
| 25 | 110 | (89.0–137) |
| 26 | 4.52 | (4.12–4.97) |
| 27 | 5.96 | (5.70–6.23) |
| 28 | 3.89 | (3.24–4.68) |
| 29 | 5.46 | (4.80–6.21) |
| 30 | 9.44 | (8.73–10.2) |
| 31 | 186 | (156–221) |
| 32 | 79.1 | (74.1–84.1) |
| 33 | 1.50 | (1.40–1.60) |
| 34 | 132 | (117–148) |
| 35 | 24.9 | (23.5–26.5) |
| 36 | 114 | (97.2–134) |
| Succinylcholine | 25.2 | (22.2–28.7) |
| Decamethonium | 101 | (85.1–119) |

Muscle relaxation action under a diabetic condition IC$_{50}$

Alloxan monohydrate (Nakarai Kagaku, Japan) was administered to the tail vein of ddY mice 4 to 5 weeks old, in a dose of 85 mg/kg, and the blood glucose level was monitored starting at the 28th day, by a glucose analyzer from the administration of alloxan (Bechmann Type II). Mice 8 to 11 weeks old and weighing 19.0 to 36.0 g, and having a blood glucose level of 310 to 460 mg/dl, were chosen and used to prepare neuromuscular preparations as described above. The results are shown in the following table.

| Example No. (Reference Example No.) | IC$_{50}$ (90% reliance) μM | |
| --- | --- | --- |
| 1 | 25.9 | (21.7–30.8) |
| 5* | 107 | (97.5–116) |
| 2 | 32.7 | (28.6–37.3) |

| Example No. (Reference Example No.) | IC$_{50}$ (90% reliance) μM | |
| --- | --- | --- |
| 18 | 51.1 | (48.0–54.5) |
| 20 | 21.7 | (20.1–23.5) |
| 21 | 7.66 | (6.93–8.45) |
| 22 | 21.8 | (20.9–22.6) |
| 23 | 11.9 | (10.7–13.2) |
| Succinylcholine | 19.3 | (17.4–21.4) |
| Decamethonium | 131 | (123–141) |

We claim:

1. A quaternary ammonium compound represented by the formula (I):

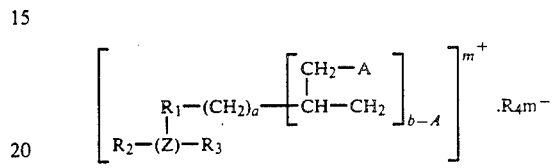

wherein R$_1$ represents —CH$_2$—, a lower alkyleneoxy, a lower alkenylene, a lower alkynylene, —CO—, —COO—, a lower alkylene carbonyloxy, —CH(OR$_5$)—, a lower alkylenecarbonyl, a hydroxy lower alkylene, —O—, —S—, —SO—, or —SO$_2$—;

R$_2$ represents a hydrogen atom, a hydroxy lower alkyl, an aldehyde, a lower alkyl carbonyl, —NO$_2$, or —NHR$_6$;

R$_3$ represents a hydrogen atom of a group —R$_1$—(CH$_2$)$_a$—[CH(CH$_2$A)—CH$_2$]$_b$—A;

R$_4$ represents an anion selected from the group consisting of chloride, bromide, iodide, sulfate, sulfite, phosphate, tosylate, citrate, succinate, acetate and malate;

R$_5$ and R$_6$ represent a hydrogen atom or acetyl;

A represents a quaternary ammonium group formed from a member selected from the group consisting of trimethyl ammonium, triethyl ammonium, methyl diethyl ammonium, tripropyl ammonium, N-methylmorpholino, tropine derivatives, pyridino, quinolino and thiazolino;

a represents an integer of 1 to 8;

b represents 0 or 1;

m represents an integer of 1 to 4; and (Z) represents a trivalent benzene ring.

2. A compound according to claim 1 wherein R$_1$ represents —CO$_2$—, —CH$_2$O—, —C≡C—, —CO—, —COO—, CH$_2$COO—, —CH(OR$_5$)—, —CH$_2$CO—, —CH$_2$CH(OH—, —O—, —S—, —SO— or —SO$_2$—; R$_2$ represents a hydrogen atom, —CH$_2$OH, —CH(CH$_3$)OH, —CH(C$_2$H$_5$)OH, —CHO, —COC$_2$H$_5$, —NO$_2$ or NHR$_6$; and other symbols have the same meaning as defined under the formula (I).

3. A compound to claim 1 which is 1,4-bis(6-triethylammoniohexyl)-2-nitrobenze diiode.

4. A pharmaceutical preparation for muscle relaxation comprising a compound according to claim 1 together with a conventional pharmaceutical carrier.

* * * * *